(12) United States Patent
Mann et al.

(10) Patent No.: US 12,582,400 B2
(45) Date of Patent: Mar. 24, 2026

(54) SYSTEMS, DEVICES, AND METHODS FOR ENDOSCOPE OR LAPAROSCOPE MAGNETIC NAVIGATION

(71) Applicant: G.I. Windows, Inc., Westwood, MA (US)

(72) Inventors: Shani Mann, Needham, MA (US);
Dane T. Seddon, Boston, MA (US);
Roman I. Kats, Chula Vista, CA (US)

(73) Assignee: G.I. Windows, Inc., Canton, MA (US)

( * ) Notice: Subject to any disclaimer, the term of this patent is extended or adjusted under 35 U.S.C. 154(b) by 89 days.

(21) Appl. No.: 18/769,695

(22) Filed: Jul. 11, 2024

(65) Prior Publication Data

US 2025/0009354 A1     Jan. 9, 2025

Related U.S. Application Data

(63) Continuation of application No. 18/241,535, filed on Sep. 1, 2023, now Pat. No. 12,053,181.

(60) Provisional application No. 63/403,543, filed on Sep. 2, 2022.

(51) Int. Cl.
| | |
|---|---|
| *A61B 17/11* | (2006.01) |
| *A61B 34/00* | (2016.01) |
| *A61B 17/00* | (2006.01) |

(52) U.S. Cl.
CPC .............. *A61B 17/11* (2013.01); *A61B 34/73* (2016.02); *A61B 2017/00296* (2013.01); *A61B 2017/00876* (2013.01); *A61B 2034/731* (2016.02)

(58) Field of Classification Search
CPC . A61B 17/11; A61B 34/73; A61B 2017/0409; A61B 2034/731; A61B 17/3468; A61B 5/6851; A61F 2/966; A61F 2/95; A61F 2/962
See application file for complete search history.

(56) References Cited

U.S. PATENT DOCUMENTS

| | | | | |
|---|---|---|---|---|
| 6,264,662 B1 * | 7/2001 | Lauterjung | ............... | A61F 2/95 |
| | | | | 623/1.11 |
| 2013/0253309 A1 * | 9/2013 | Allan | ........................ | A61B 6/00 |
| | | | | 604/95.01 |
| 2014/0277342 A1 * | 9/2014 | Roeder | ................... | A61F 2/966 |
| | | | | 623/1.11 |

* cited by examiner

*Primary Examiner* — Darwin P Erezo
*Assistant Examiner* — Christina C Lauer
(74) *Attorney, Agent, or Firm* — Nutter McClennen & Fish LLP

(57) ABSTRACT

Various embodiments incorporate an "end effector" in a magnetic anastomosis device system. The end effector is located between the handle of an endoscope or laparoscope and the distal end of the catheter. The end effector engages with and secures the magnetic anastomosis device assembly within a body lumen. The end effector is able to hold a magnetic device or devices with a tensile strength of 0-10 lbs. The end effector is small enough that two instruments of 1.8 mm diameter or smaller may be placed in a 3.7 mm working channel of an endoscope.

17 Claims, 37 Drawing Sheets

ENDOSCOPE

CONTROL
APPARATUS
MEMBER

MAGNET
MEMBER

CAP
MEMBER

Shaft    Spring    Clutch    Pulley & string

Pulley and
clutch
apparatus

Cap and sutures

"Finishing rail"
Controlled by three sutures

Basket and sutures

Balloon and sutures

SUTURE'S
MAGNET

STRING
MEMBER (A)

Hook option (B)

SYSTEMS, DEVICES, AND METHODS FOR ENDOSCOPE OR LAPAROSCOPE MAGNETIC NAVIGATION

CROSS-REFERENCE TO RELATED APPLICATION(S)

This patent application is a continuation of U.S. patent application Ser. No. 18/241,535 entitled SYSTEMS, DEVICES, AND METHODS FOR ENDOSCOPE OR LAPAROSCOPE MAGNETIC NAVIGATION filed Sep. 1, 2023, which claims the benefit of U.S. Provisional Patent Application No. 63/403,543 entitled SYSTEMS, DEVICES, AND METHODS FOR ENDOSCOPE OR LAPAROSCOPE MAGNETIC NAVIGATION filed Sep. 2, 2022, each of which is hereby incorporated herein by reference in its entirety.

FIELD OF INVENTION

The invention relates to deployable magnetic compression devices, and, more particularly, to systems, devices, and methods for the delivery, deployment, and positioning of magnetic compression devices at a desired site so as to improve the accuracy of anastomoses creation between tissues, organs, or the like.

BACKGROUND

Bypasses of the gastroenterological (GI), cardiovascular, or urological systems are typically formed by cutting holes in tissues at two locations and joining the holes with sutures or staples. A bypass is typically placed to route fluids (e.g., blood, nutrients) between healthier portions of the system, while bypassing diseases or malfunctioning tissues. The procedure is typically invasive, and subjects a patient to risks such as bleeding, infection, pain, and adverse reaction to anesthesia. Additionally, a bypass created with sutures or staples can be complicated by post-operative leaks and adhesions. Leaks may result in infection or sepsis, while adhesions can result in complications such as bowel strangulation and obstruction. While traditional bypass procedures can be completed with an endoscope, laparoscope, or robot, it can be time consuming to join the holes cut into the tissues. Furthermore, such procedures require specialized expertise and equipment that is not available at many surgical facilities.

As an alternative to sutures or staples, surgeons can use mechanical couplings or magnets to create a compressive anastomosis between tissues. For example, compressive couplings or paired magnets can be delivered to tissues to be joined. Because of the strong compression, the tissue trapped between the couplings or magnets is cut off from its blood supply. Under these conditions, the tissue becomes necrotic and degenerates, and at the same time, new tissue grows around points of compression, e.g., on the edges of the coupling. With time, the coupling can be removed, leaving a healed anastomosis between the tissues.

Nonetheless, the difficulty of placing the magnets or couplings limits the locations that compressive anastomosis can be used. In most cases, the magnets or couplings have to be delivered as two separate assemblies, requiring either an open surgical field or a bulky delivery device. For example, existing magnetic compression devices are limited to structures small enough to be deployed with a delivery conduit e.g., an endoscopic instrument channel or laparoscopic port. When these smaller structures are used, the formed anastomosis is small and suffers from short-term patency. Furthermore, placement of the magnets or couplings can be imprecise, which can lead to anastomosis formation in locations that is undesirable or inaccurate.

Modern endoscopic surgical practices often require working with multiple instruments due to endoscopic working channel size limitations. Working with multiple instruments adds procedural steps, increases procedure time, and requires additional effort on the part of clinicians. This increases the risk to the patient due to longer surgery times and increased risk of bleeding.

Thus, there still remains a clinical need for reliable devices and minimally invasive procedures that facilitate compression anastomosis formation between tissues in the human body in as few steps as possible.

SUMMARY

In accordance with one embodiment, an apparatus for guiding magnetic anastomosis devices comprises a metal cord having a distal end and a proximal end configured to fit within a catheter, wherein the distal end is bent substantially at a 180° angle, such that the distal end of the metal cord is pointed toward the proximal end, forming a bent portion of the metal cord; wherein the bent portion of the metal cord is configured to engage a magnetic anastomosis device; wherein a first pulling force on the metal cord is greater than a second force needed to unbend the metal cord outside of the catheter; and wherein the first pulling force is less than a third force needed to unbend the metal cord inside of the catheter due to a friction force between the metal cord and a catheter wall.

In various alternative embodiments, the metal cord may be less than or equal to 1.8 mm in diameter. The bent portion of the metal cord may be able to hold a magnetic device or devices with a tensile strength of 0-10 pounds. The friction force may be reduced to zero when the bent portion of the metal cord is disengaged from the catheter. The bent portion may be unbent in order to disengage the magnetic anastomosis device, e.g., the bent portion of the metal cord may unbend after disengaging from the catheter to release the magnetic device.

Embodiments may include a first ferrule configured to engage with the distal end of the metal cord such that the metal cord and ferrule are engaged with the catheter wall. Embodiments additionally may include a second ferrule configured to engage with the magnetic anastomosis device so as to maintain the magnetic anastomosis device within the catheter. Such embodiments may include a first magnet attached to a proximal end of the first ferrule and a second magnet attached to a distal end of the second ferrule. A string on the magnetic anastomosis device may include a first hook and the second ferrule may include a second hook wherein the first hook and the second hook are configured to interlock.

Embodiments may further include the catheter (e.g., an endoscope having a 3.7 mm working channel). Additionally or alternatively, embodiments may further include the magnetic anastomosis device (e.g., a self-assembling magnetic anastomosis device having a plurality of magnetic segments that self-assemble into, e.g., a polygon or circle configuration). The self-assembling magnetic anastomosis device may be delivered via the catheter and, when released from the catheter, may self-assemble when the bent portion of the metal cord is disengaged from the catheter. Embodiments may include a first ferrule configured to engage with the distal end of the metal cord such that the metal cord and ferrule are engaged with the catheter wall. Embodiments additionally may include a second ferrule configured to engage with the magnetic anastomosis device so as to maintain the magnetic anastomosis device within the catheter.

Additional embodiments may be disclosed and claimed.

BRIEF DESCRIPTION OF THE DRAWINGS

Those skilled in the art should more fully appreciate advantages of various embodiments of the invention from the following "Description of Illustrative Embodiments," discussed with reference to the drawings summarized immediately below.

It should be noted that the foregoing figures and the elements depicted therein are not necessarily drawn to consistent scale or to any scale. Unless the context otherwise suggests, like elements are indicated by like numerals. The drawings are primarily for illustrative purposes and are not intended to limit the scope of the inventive subject matter described herein.

DESCRIPTION OF ILLUSTRATIVE EMBODIMENTS

Various embodiments incorporate an "end effector" in a magnetic anastomosis device system or coupling mechanism system. The end effector is located between the proximal end of a delivery device such as a catheter, endoscope, or laparoscope and the distal end of the delivery device. The end effector engages with and secures the magnetic anastomosis device assembly within a delivery device lumen. In certain embodiments, the end effector is able to hold a magnetic device or devices with a tensile strength of 0-10 lbs. In certain embodiments, the end effector is small enough that two instruments of 1.8 mm diameter or smaller may be placed in a 3.7 mm working channel or smaller of delivery device such as an endoscope.

Figure 22:
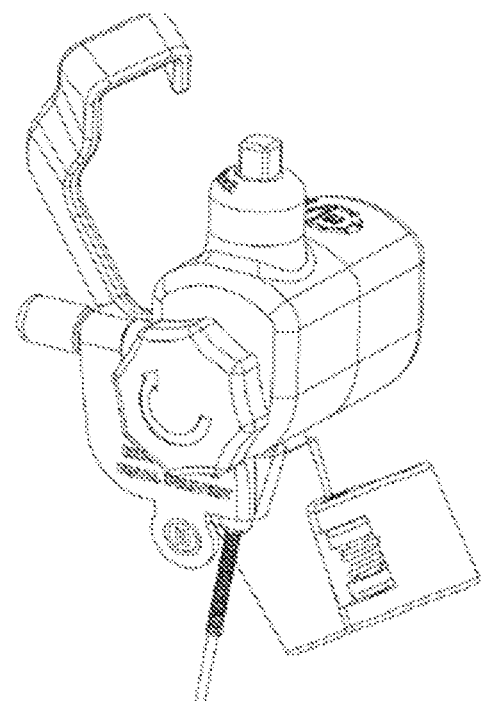
FIG. 22 depicts a trans oral delivery device for a magnetic compression anastomosis device.

FIG. 22 schematically shows a trans oral delivery device for delivering a self-forming magnetic compression anastomosis device into the gastrointestinal tract. The magnet member is delivered via a standard flexible endoscope with a delivery device to a target anatomical site for creation of an anastomosis. While in the delivery device, the magnetic compression anastomosis device is in a linear configuration. After exiting the delivery device, the magnetic compression anastomosis device forms into a polygonal shape due to the polarity of the magnetic wedge members, as shown in FIG. 23.

Figure 23:
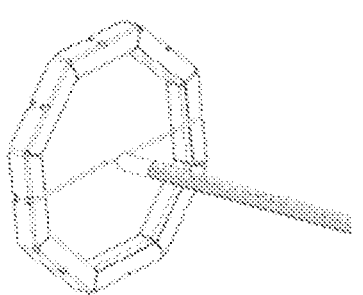
FIG. 23 depicts a delivery device controlling a magnetic anastomosis device.

The delivery device itself may be used to control the magnetic anastomosis device, as is shown in FIG. 23. The delivery device may be designed to allow for easy manipulation of the magnet and control release of the magnet.

Figure 24:
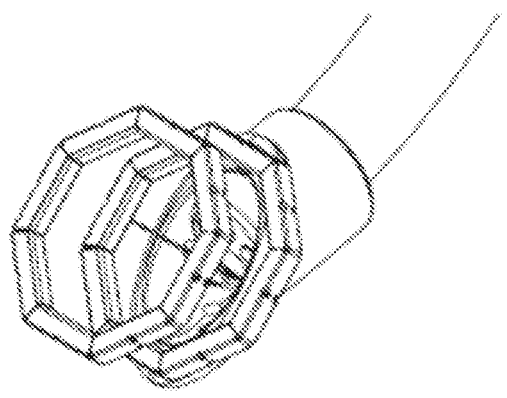
FIG. 24 depicts a delivery device working with another tool to hold a second magnetic anastomosis device.

FIG. 24 schematically shows the delivery device working simultaneously with another tool holding a second magnetic anastomosis device to couple the magnets and form an anastomosis.

Figure 25:
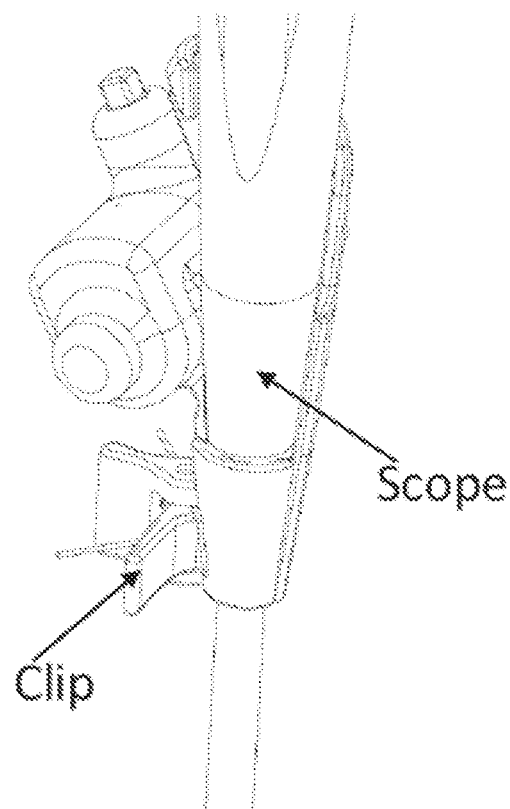
FIG. 25 depicts a clip member for attaching a trans oral delivery device to an endoscope.

FIG. 25 schematically shows a clip member for quick and secure mounting of the trans oral delivery device to an endoscope. The clip member may be quickly attached to and detached from the endoscope allowing for ease of use of the delivery device with an endoscope.

Figure 26:
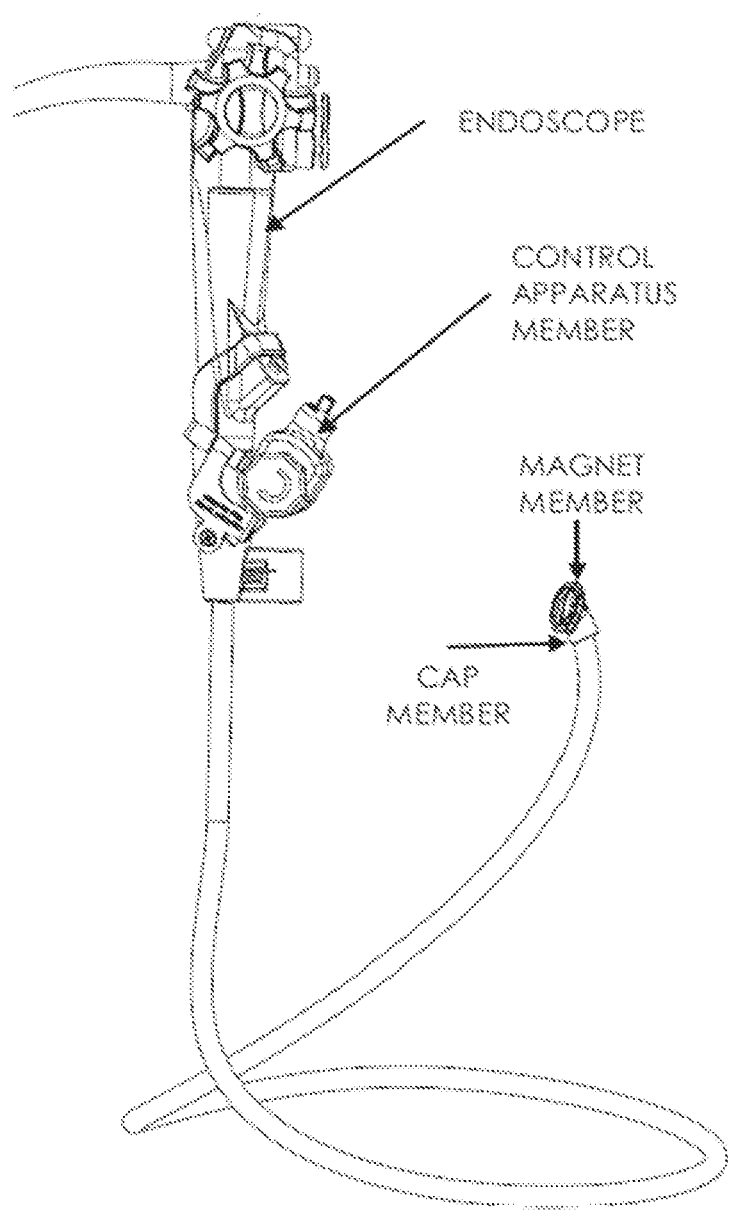
FIG. 26 depicts a trans oral delivery device mounted on an endoscope.

FIG. 26 schematically shows the trans oral delivery device mounted on an endoscope. The delivery device comprises a control apparatus member, a tube member, and a magnet device. The connection between the magnet and the control apparatus is made through the tube member which inserts into the working channel of an endoscope. The control apparatus member allows the clinician the ability to control a magnet member located on the distal end of the endoscope. The control apparatus member also allows the clinician to release the magnet member away from the distal end of the delivery device, but within control for review of the anastomosis site before deployment of the magnet using a two-step operation.

Figure 27:
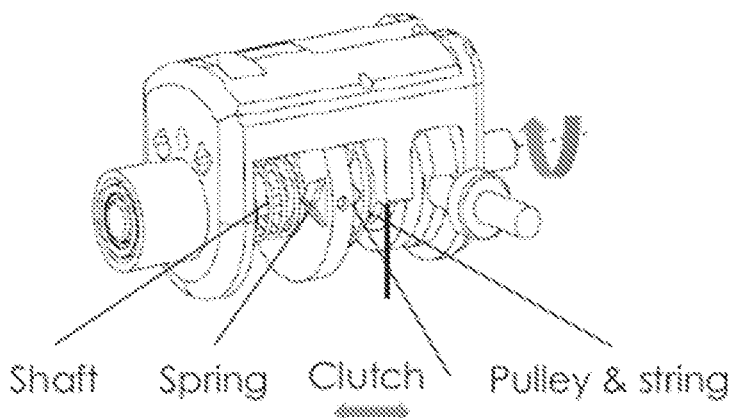
FIGS. 27, 28, and 29 depict alternate views of a control member apparatus.
Figure 28:
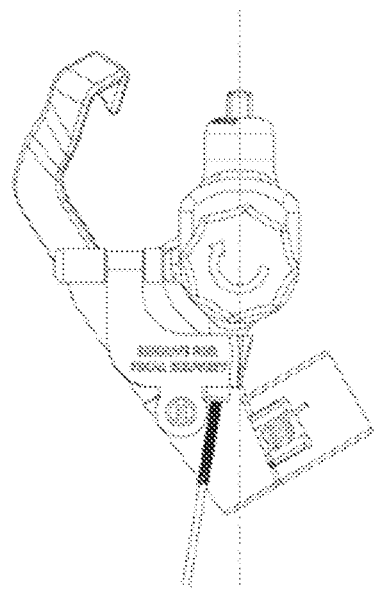
Figure 29:
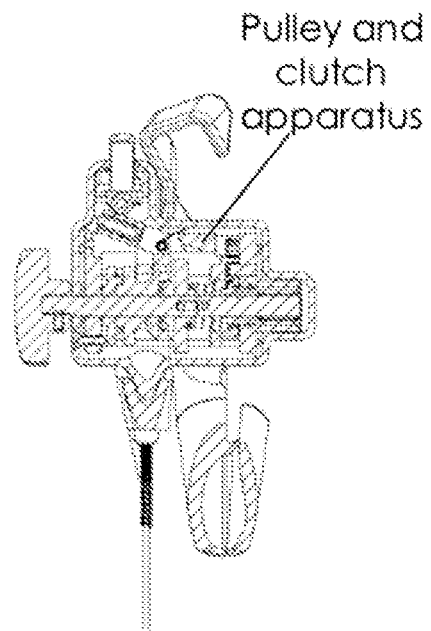
Figure 30:
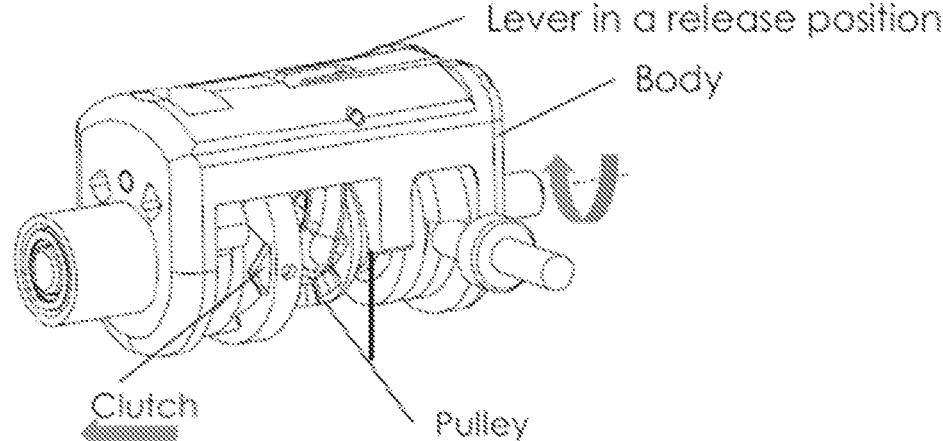
FIGS. 30, 31, 32, and 33 depict alternate views of an apparatus for releasing the clutch of a control member apparatus.
Figure 31:
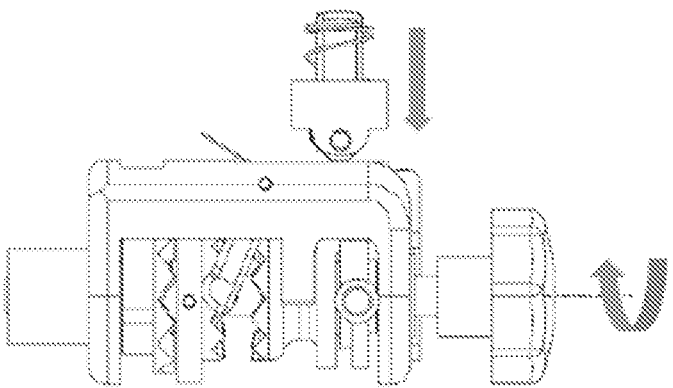
Figure 32:
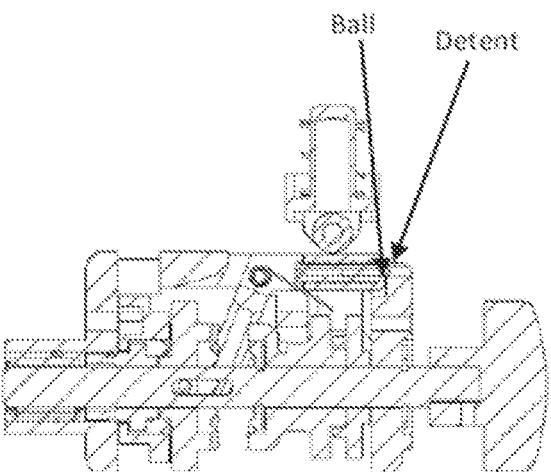
Figure 33:
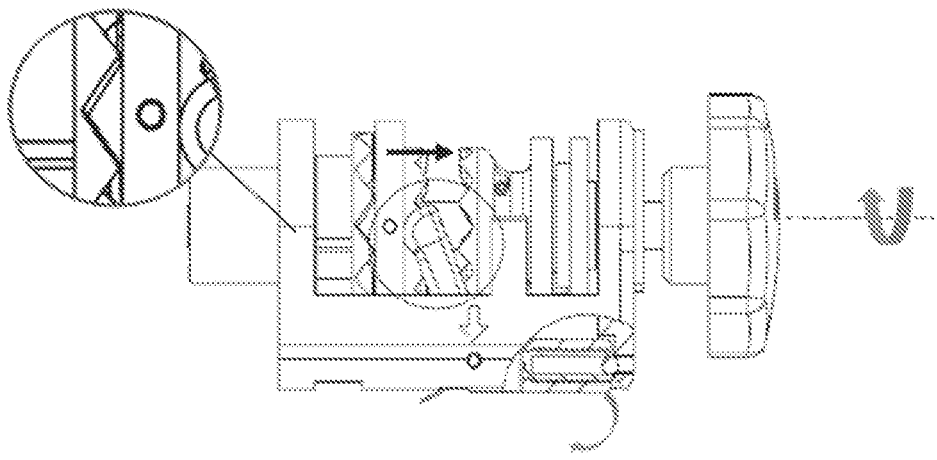
Figure 34:
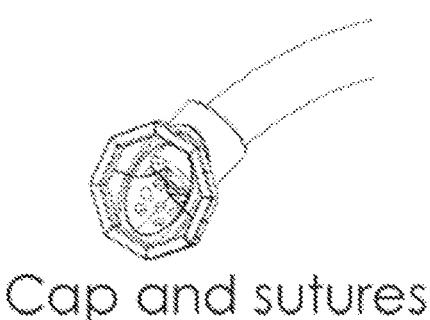
FIG. 34 depicts various embodiments of control mechanisms for magnetic anastomosis devices.
Figure 34:
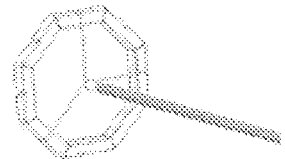
Figure 34:
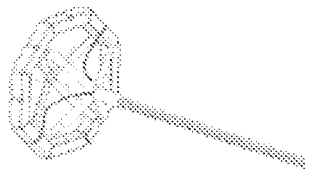
Figure 34:
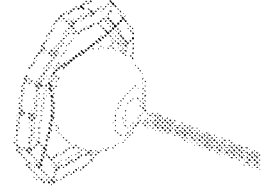

FIGS. 27, 28, and 29 schematically show varying views of the pulley and clutch apparatus of the control apparatus member. The pulley pulls tension in the system to control the magnet. The clutch limits the tension in the system for safety. The clutch is capable of moving back and forth through a slot in the shaft. The string attached to the pulley may be pulled or released by turning the knob. The spring is designed to hold the clutch and pulley together until the force exceeds the spring force. After the force exceeds the spring force, the spring compresses and the clutch is pulled off of the pulley and the pulley stops rotating. FIG. 27 shows the apparatus wherein the clutch is pulled from the pulley and locked so that the pulley holding the magnet may move freely. The clinician may press a button which presses a lever member that pushes the clutch. The level member comprises a ball and detent on the body. As the clinician presses the lever down, the ball locks inside the detent on the body and the apparatus is locked in the release position.

FIGS. 30, 31, 32, and 33 schematically show varying views of the apparatus for releasing the clutch member. The release clutch comprises teeth that push the clutch toward the pulley as the clinician rotates the shaft. The force of pushing the clutch also pushes the lever member and releases the clutch member from the locking position.

FIGS. 34(A)-34(D) schematically show various non-limiting embodiments of controlling a magnet at the distal end of an endoscope to allow for manipulation and alignment of magnetic compression anastomosis devices. The control methods also allow for changing of the presentation angle for transluminal mating with the assistance of an endoscope. Non-limiting examples of control mechanisms include a cap and sutures, "finishing rail" controlled by three sutures, a basket and sutures, and a balloon and sutures.

Various embodiments of the invention comprise an end effector system that holds a magnetic compression anastomosis device preferably with a 0-10 lbs. tensile strength. The end effector is located between the proximal end of the delivery device and the distal end of the delivery device. The end effector comprises a cord (e.g., typically a metal cord, although the cord could be another material such as a suture or string), which, upon release of the cord, the magnetic compression anastomosis device will be released and self-assemble. The end effector may also engage and secure the magnetic device. This system is preferably small enough that two instruments of 1.8 mm diameter or less may be placed in a 3.7 mm or less endoscope working channel. This decreases risk to the patient and increases success rate of the operation.

Figure 35:
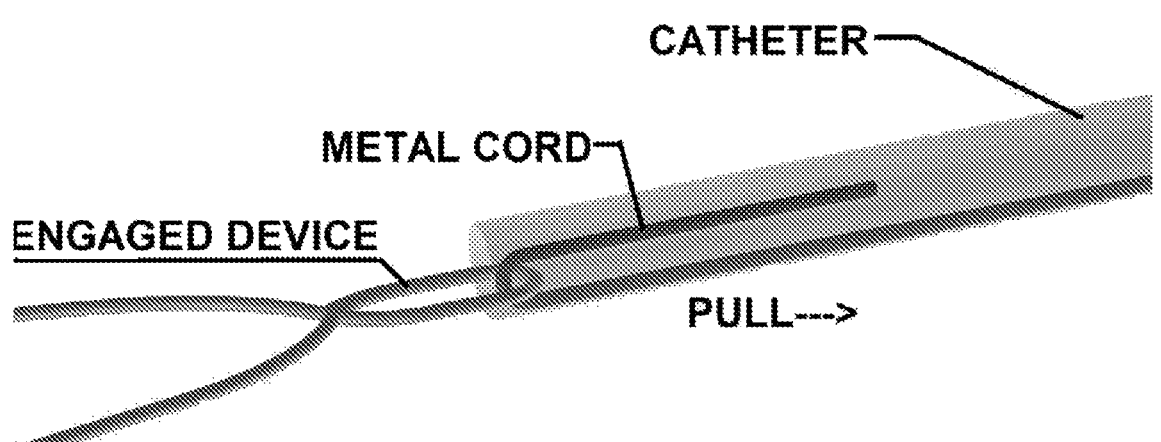
FIG. 35 depicts an end effector comprising a thin metal cord inside a tube and engaged with magnet or coupling mechanism.

FIG. 35 schematically shows a non-limiting example of an end effector comprising a bent metal cord inside the distal end of a catheter and engaged with a magnet or coupling mechanism. The metal cord within the catheter is bent substantially at a 180° angle such that the distal end of the metal cord is pointed toward the proximal end as shown in FIG. 35. The bent metal cord keeps the magnetic device engaged with the cord as the cord is held inside the catheter. The pulling force within the catheter is smaller than the combined force to unbend the metal cord within the catheter given the friction force between the metal cord and the catheter wall. However, the pulling force is larger than the force needed to unbend the metal cord outside of the catheter. The friction force is zero after the bent portion of the metal cord is disengaged from the catheter. After disengaging from the catheter, the bent portion of the metal cord unbends, releasing the magnetic device.

Figure 36:
FIG. 36 depicts an end effector of FIG. 35 engaged with a magnetic anastomosis device.

FIG. 36 schematically shows an end effector of FIG. 35 engaged with a magnetic compression anastomosis device while the bent portion of the metal cord is engaged within the catheter. This allows for control of the magnetic device within the body lumen.

Figure 37:
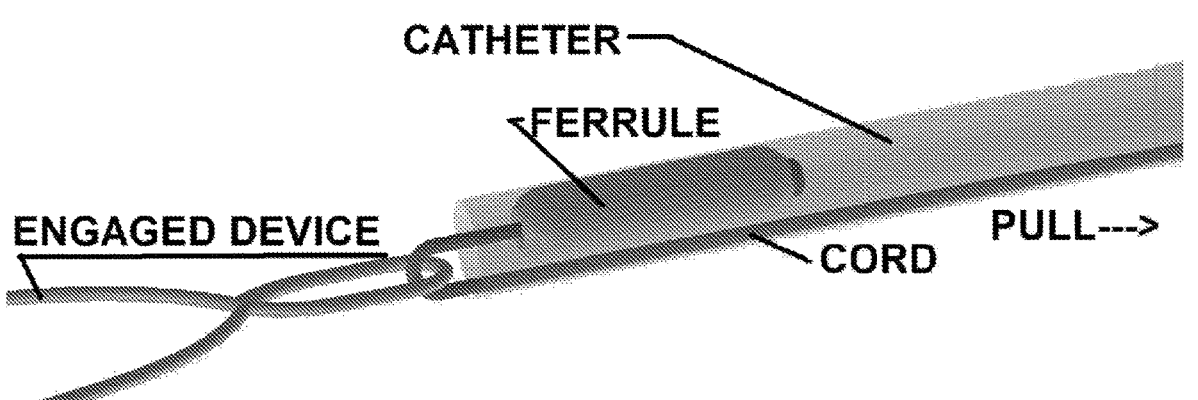
FIG. 37 depicts an end effector comprising a single ferrule, a fold cord, and engaged with magnet or coupling mechanism.

FIG. 37 schematically shows an end effector comprising a single ferrule, a fold cord, and engaged with magnet or coupling mechanism. While within the catheter, the ferrule keeps the cord engaged with the catheter due to increased friction. After the ferrule and bent portion of the metal cord disengage from the catheter, the metal cord will unbend and release the ferrule.

Figure 38:
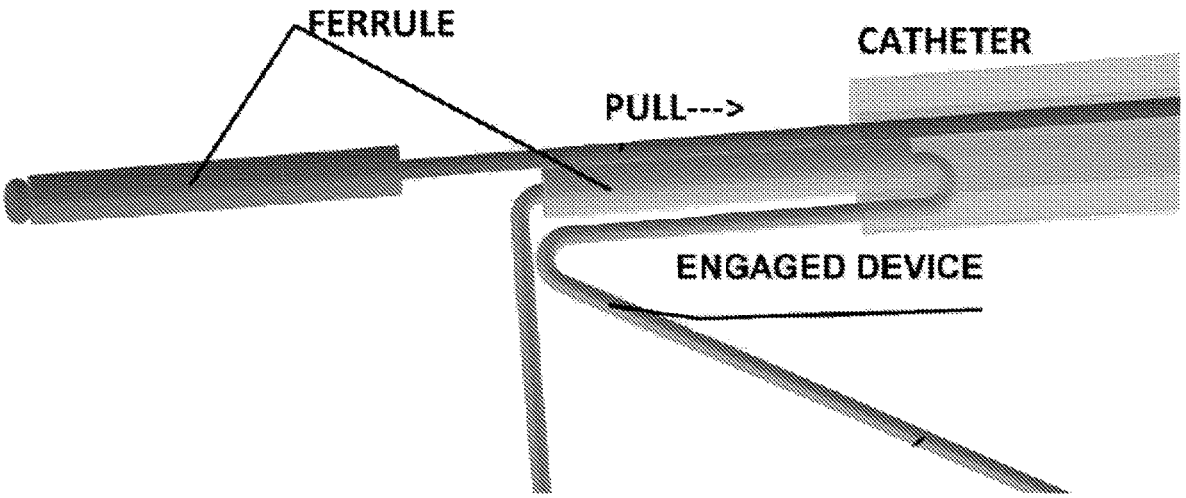
FIG. 38 depicts an end effector comprising a pair ferrule, a straight cord, and engaged with magnet or coupling mechanism.

FIG. 38 schematically shows an end effector comprising a pair ferrule, a straight cord, and engaged with magnet or coupling mechanism. The ferrule on the metal cord keeps the ferrule on the device within the catheter until release of the device.

Figure 39:
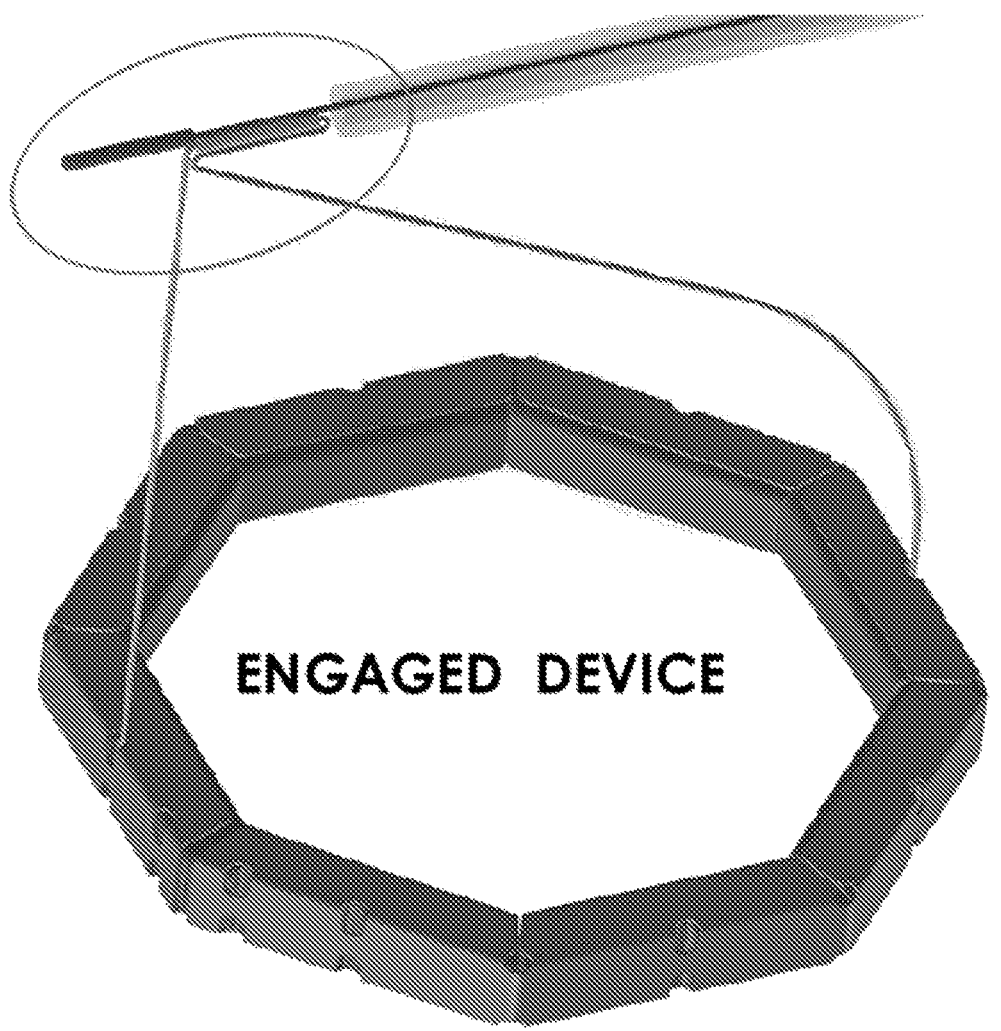
FIG. 39 depicts an end effector of FIG. 38 engaged with a magnetic anastomosis device.

FIG. 39 schematically shows an extended view of the double ferrule end effector of FIG. 38 engaged with a magnetic compression anastomosis device.

Figure 40:
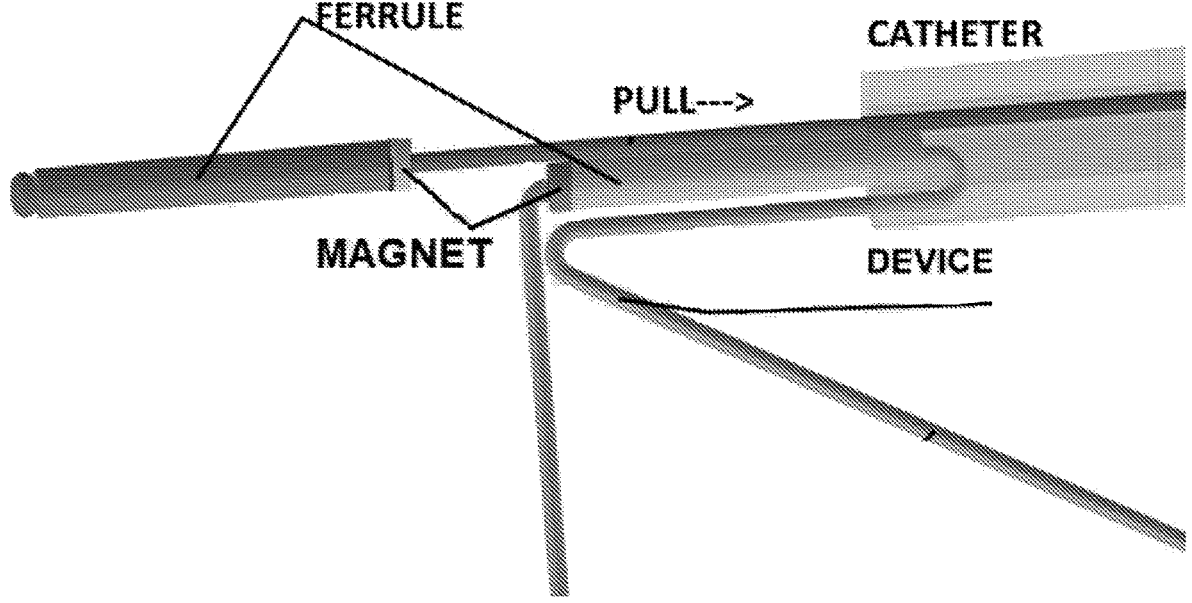
FIG. 40 depicts an end effector comprising a pair ferrule with magnets, a straight cord, and engaged with magnet or coupling mechanism.

FIG. 40 schematically shows an end effector comprising a pair ferrule with magnets, a straight cord, and engaged with magnet or coupling mechanism. The system comprises a magnet at the proximal end of the ferrule engaged with the metal cord, and a magnet at the distal end of the ferrule engaged with the magnetic device. The magnet on the ferrule at the distal end of the metal cord is capable of catching the magnet on the already released ferrule of the magnetic device. This allows for control and securement of the magnetic device at the proper anastomosis site. The connection between the string on the magnetic device and the magnet on the attached ferrule may be made in various ways. The magnetic device will always be connected to the control apparatus while inside the catheter.

Figure 41:
FIG. 41 depicts an end effector comprising a pair hook mechanism, a straight cord and engaged with magnet or coupling mechanism.
Figure 41:

FIGS. 41(A)-41(B) schematically show an end effector comprising a pair hook mechanism, a straight cord, and engaged with magnet or coupling mechanism. A hook may be attached to the string member of the magnetic anastomosis device. The hook is capable of engaging another hook attached to sutures on the ferrule magnet. While inside the catheter, the hooks will engage, and will disengage after exiting the catheter, releasing the magnetic anastomosis device from the ferrule and delivery device.

It should be noted that self-assembling magnetic anastomosis addresses several of the historical disadvantages of traditional anastomosis such as allowing a surgical-quality anastomosis in a minimally-invasive fashion using devices that reproducibly re-assemble into a larger magnet structure of a predetermined shape in vivo. The constraints imposed by the described embodiments are designed to allow the devices to consistently self-assemble into the correct shape upon deployment, which greatly reduces the risks of surgical complications due to misshapen devices or premature detachment and also reduces the risks associated with surgical access and ensure that the anastomosis is formed with the correct geometric attributes. Overall, this ensures the patency of the anastomosis.

Thus, as described herein, embodiments include flexible linear magnetic devices comprising linked magnetic multipole segments that, when extruded from the end of a deployment channel or lumen, self-assemble to form a rigid, multipolar polygonal ring magnet (PRM; generally "magnetic device"). The self-assembly is directed by the configuration of magnets, rollers, flex elements, and vertebra skins that is capable of returning to a pre-determined shape. Generally speaking, the physical and magnetic structure of the deployed magnetic devices is such that when two magnetic devices approach one another, there is a rapidly strengthening attractive magnetic interaction, which creates a coupling between the magnetic devices. In some instances, it is necessary to pre-align the complimentary devices, however, in other instances the devices self-align by undergoing fast in-plane rotation with respect to one another, as discussed in detail below. As described in detail below, systems including the magnetic devices may include an endoscope having sensors that allow the endoscope to sense the position of a mating magnetic device or another endoscope that will deploy the mating magnetic device.

When deployed in adjacent tissues, for example adjacent organs or different regions of the same organ, the coupled magnetic devices create a compressive ring that can be surgically opened, or allowed to form an anastomosis without further intervention. When paired devices are left alone, the compressive force against the tissues collapse the vasculature and extrude fluids in the tissues, further reducing the distance between the devices and increasing the magnetic attraction. With time, the coupled devices eventually couple completely and fall away, leaving a formed anastomosis. This cascade begins when the devices approach within "capture range," whereby their mutually-attractive forces are sufficient to align the devices, trap the intervening tissue, and resist the natural pliancy of the tissues as well as the motion of the tissue under normal physiologic function.

Overall, the design specifications of the devices depend on the patient and the intended anastomosis. The design specifications may include: required capture range, desired effective inner and outer diameters of the deployed polygonal rings (e.g., as defined by the desired anastomosis size and instrument passage), thickness of the target tissue, and the inner diameter of guiding channel and the smallest radius of curvature to which the guiding channel may be bent and through which the magnets must pass. Once the design specifications are chosen, corresponding magnetic device designs can be determined, such as polygon-side-count and length, and the maximum lateral dimensions of the flexible linear magnetic structure that will be deployed through the delivery instrument.

Figure 1:
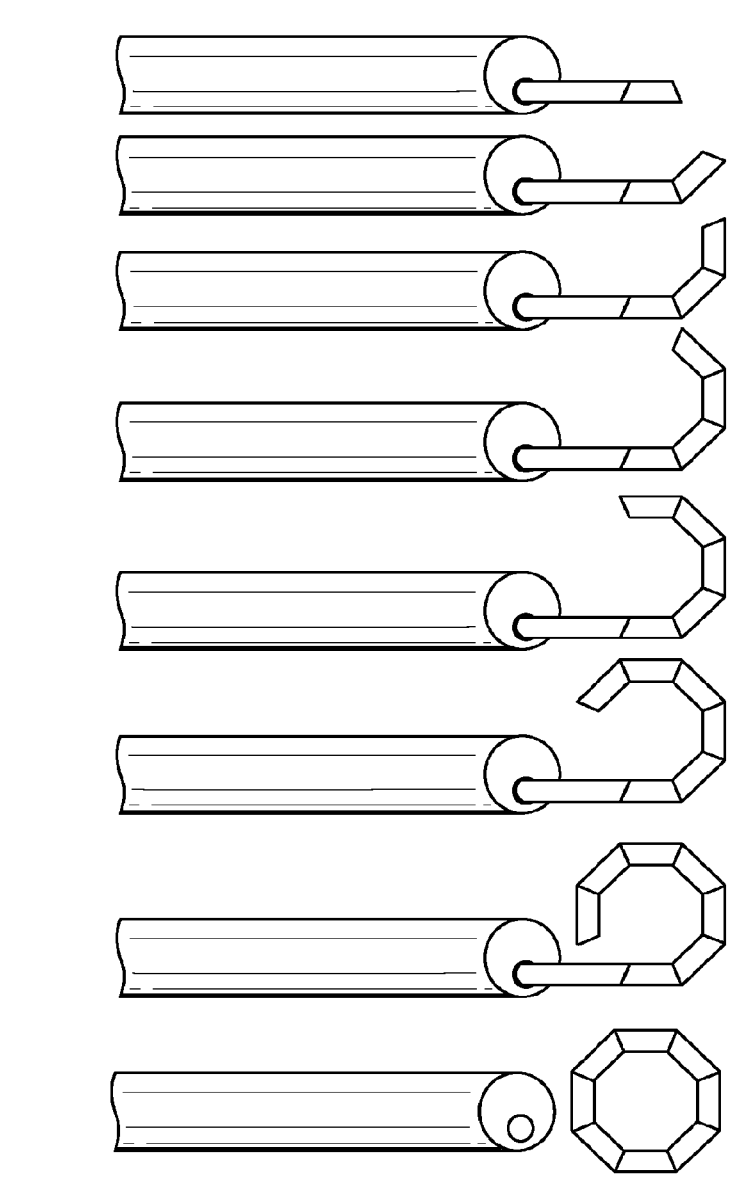
FIG. 1 shows a magnet assembly delivered through an endoscope instrument channel such that the individual magnets self-assemble into a larger magnetic structure—in this particular case, an octagon.

A magnetic compression anastomosis device (e.g., a self-assembling magnetic compression anastomosis device) may be linearly disposed with the delivery device (e.g., catheter or other delivery device) and engaged with an end effector of the types described above prior to deployment of the magnetic compression anastomosis device. Deployment of a magnetic compression anastomosis device is generally illustrated in FIG. 1. When used with the techniques described herein, the devices allow for the delivery of a larger magnetic structures than would otherwise be possible via a small delivery conduit, such as in a standard endoscope, if the devices were deployed as a completed assembly. Larger magnet structures, in turn, allow for the creation of larger anastomoses that are more robust, and achieve greater surgical success. Because the magnetic devices are generally radiopaque and echogenic, the devices generally can be positioned using fluoroscopy, direct visualization (transillumination or tissue indentation), and ultrasound, e.g., endoscopic ultrasound. The devices can also be ornamented with radiopaque paint or other markers to help identify the polarity of the devices during placement. In some embodiments, the devices can be positioned by use of sensors located in proximity to the delivery lumen and able to sense the position of a mating device, e.g., using a Reed switch or a Hall-effect sensor.

Figure 2A:
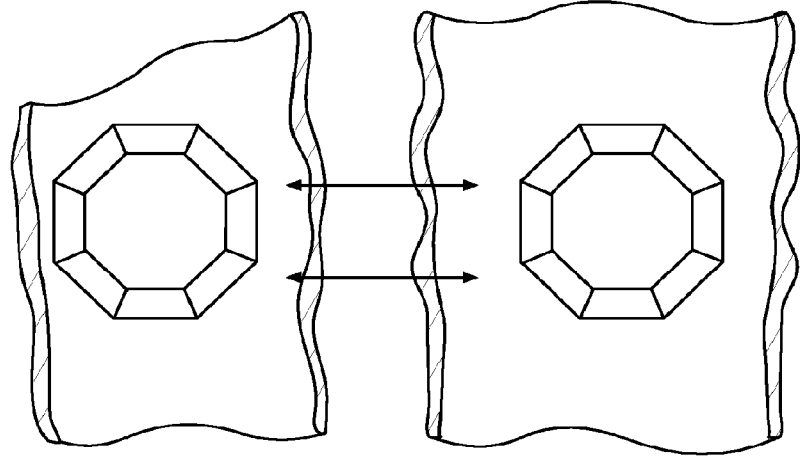
FIG. 2A shows magnet assemblies that have been delivered and deployed to adjacent tissues.
Figure 2B:
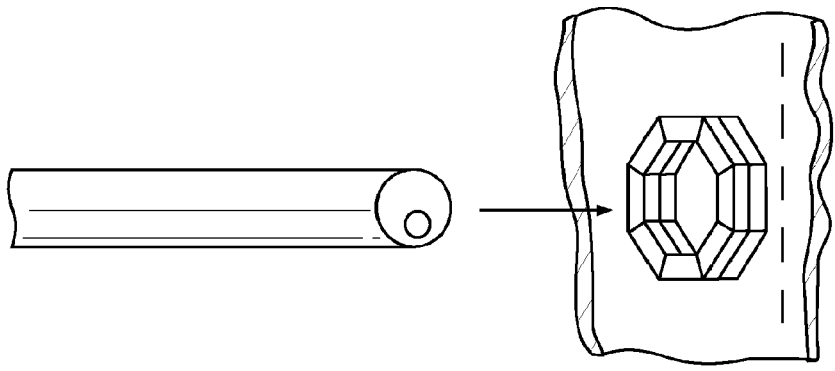
FIG. 2B shows the two magnet assemblies coupled together by magnetic attraction, capturing the intervening tissue. In some instances, the endoscope can be used to cut through the circumscribed tissue.

In general, as shown in FIG. 2A, a magnetic anastomosis procedure involves placing a first and a second magnetic structure adjacent to targeted tissues, thus causing the tissues to come together. The magnetic devices are generally deployed so that that opposite poles of the magnets will attract and bring the tissues together. The two devices may both be deployed inside the body, or one may be deployed inside the body and the other outside the body. Once the magnets have been deployed, the tissues circumscribed by the magnetic structures can be cut to provide an immediate anastomosis, as shown in FIG. 2B. In other embodiments, the tissues circumscribed by the devices will be allowed to necrose and degrade, providing an opening between the tissues. While the figures and structures of the disclosure are primarily concerned with annular or polygonal structures, it is to be understood that the delivery and construction techniques described herein can be used to make a variety of deployable magnetic structures. For example, self-assembling magnets can re-assemble into a polygonal structure such as a circle, ellipse, square, hexagon, octagon, decagon, or other geometric structure creating a closed loop. The devices may additionally include handles, suture loops, barbs, and protrusions, as needed to achieve the desired performance and to make delivery (and removal) easier.

As described with respect to the figures, a self-assembling magnetic anastomosis device can be placed with a number of techniques, such as endoscopy, laparoscopy, or with a catheter (e.g., not with direct visualization, fluoro, etc.). Regardless of method of device delivery, it is important to note that the procedure for creating the anastomosis can be terminated without perforation of tissue after confirmation of magnet coupling. As described previously, the compression anastomosis process can be allowed to proceed over the ensuing days, resulting in the natural formation of an opening between the tissues. The fused magnets can either be allowed to expel naturally or the magnets can be retrieved in a follow-up surgical procedure. Alternatively, if immediate bypass is required, the tissues circumscribed by the magnets can be cut or perforated. Perforation can be accomplished with a variety of techniques, such as cautery, microscalpel, or balloon dilation of tissue following needle and guidewire access.

Figure 3:
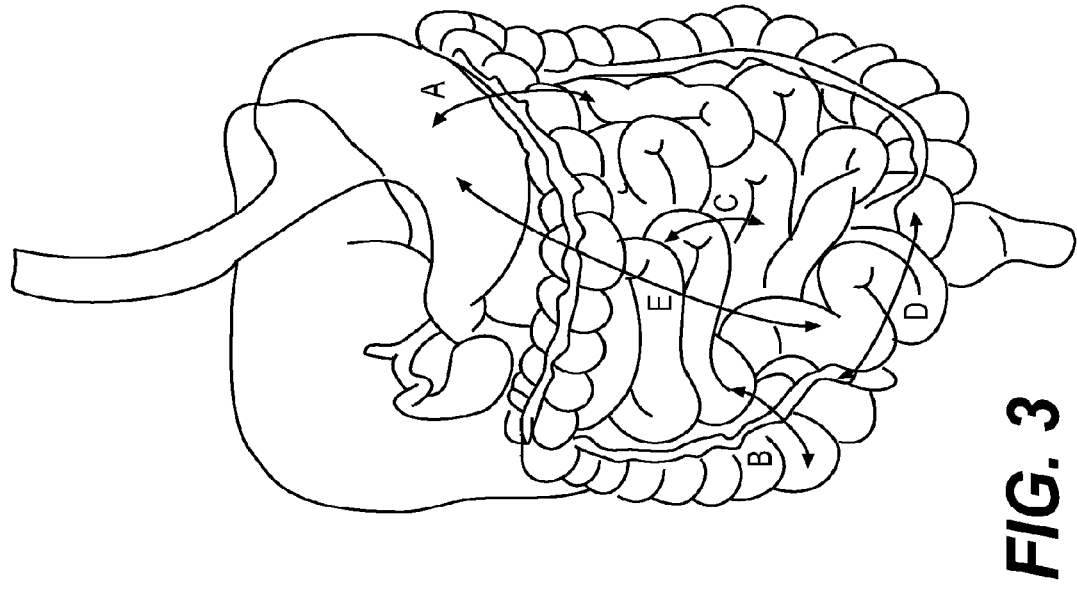
FIG. 3 shows several potential anatomical targets for anastomosis formation: Arrow A is stomach to small intestine, Arrow B is small intestine to large intestine, Arrow C is small intestine to small intestine, Arrow D is large intestine to large intestine, and Arrow E is stomach to large intestine.
Figure 4A:
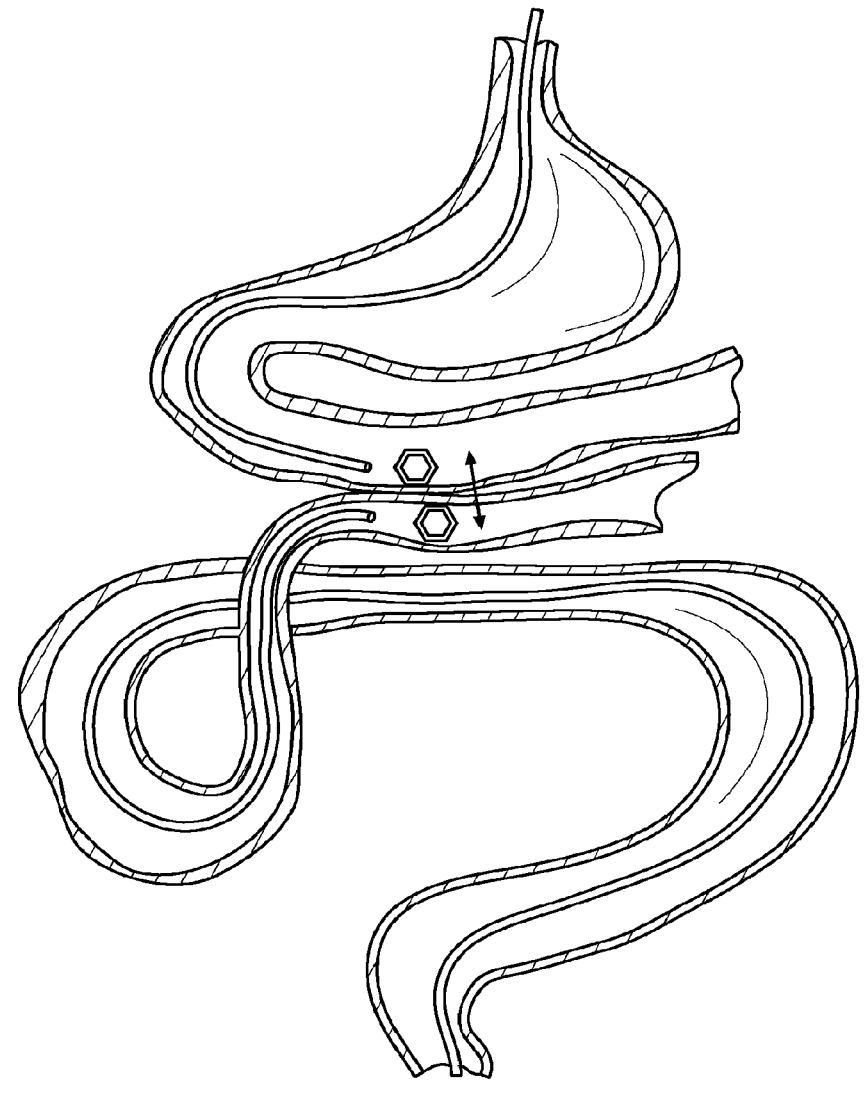
FIG. 4A shows one embodiment of delivery using two endoscopes (colonoscope and enteroscope or gastroscope) to deliver magnet assemblies.
Figure 4B:
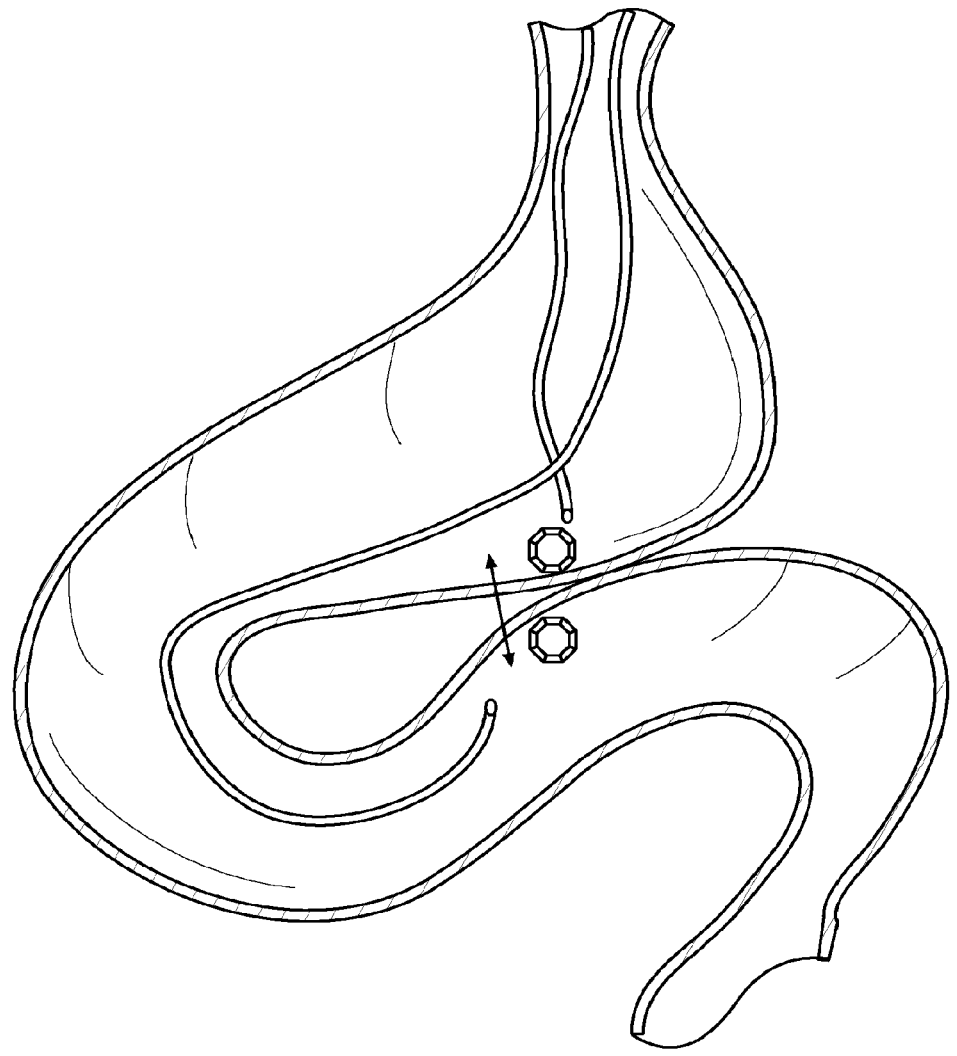
FIG. 4B shows another embodiment of delivery using two upper endoscopes both sharing per-oral entry to deliver magnet assemblies.
Figure 5:
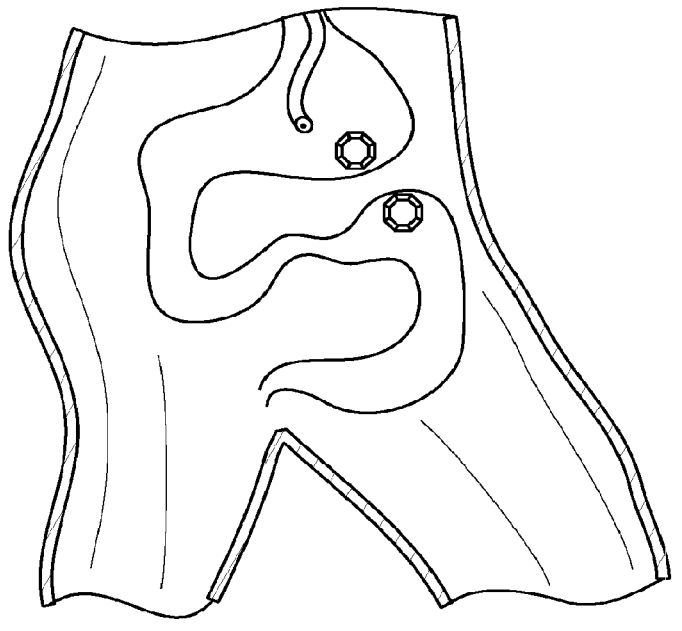
FIG. 5 shows another embodiment of delivery using a single endoscope to sequentially deliver magnet assemblies.

In some embodiments, the self-assembling magnetic devices are used to create a bypass in the gastrointestinal tract. Such bypasses can be used for the treatment of a cancerous obstruction, weight loss or bariatrics, or even treatment of diabetes and metabolic disease (i.e. metabolic surgery). Such a bypass could be created endoscopically, laparoscopically, or a combination of both. FIG. 3 illustrates the variety of gastrointestinal anastomotic targets that may be addressed with the devices of the invention: stomach to small intestine (A), stomach to large intestine (E), small intestine to small intestine (C), small intestine to large intestine (B), and large intestine to large intestine (D). In an endoscopic procedure, the self-assembling magnetic devices can be delivered using two simultaneous endoscopes, e.g., an upper endoscope or enteroscope residing in the upper small intestine, and a colonoscope residing in the lower small intestine, as shown in FIG. 4A. Alternatively, as shown in FIG. 4B, two simultaneous upper endoscopes (e.g., one residing in the stomach and the second in the small intestine) can be used to place the devices. In other embodiments, the self-assembling magnets can be delivered sequentially through the same endoscope, which has been moved between a first deployment position and a second deployment position. For example, in FIG. 4A, a single per-oral endoscope could deliver and deploy one self-assembling magnet in the small intestine, withdraw, and then deploy the second reciprocal magnet in the stomach. Again, magnet coupling could be confirmed using fluoroscopy. FIG. 5 illustrates removal of a single endoscope after placement of two magnetic devices.

A variety of techniques can be used to detect the first deployed magnetic device to assist placement of the second mating structure. Once the first device is deployed at the desired anastomotic location, the two deployed magnetic devices need to find one another's magnetic field so that they can mate and provide the compressional force needed to prompt formation of an anastomosis. Ideally, the devices can be roughly located within several cm of one another (e.g., using ultrasound), at which point the magnets should self-capture and self-align. Where this is not possible, other techniques such as one of the following techniques can be used. A first location technique involves a direct contact method using two endoscopes. Here an endoscope's displacement in an adjacent lumen creates a displacement seen by another endoscope in the adjacent lumen. The displacement identifies a potential intersection point for an anastomosis location. For example, a magnetic deployment tool (described below) will be deflected by the presence of a deployed device on the other side of a tissue wall.

The second location technique involves trans-illumination, whereby high intensity light from one endoscope is directed at the lumen wall of the proposed anastomosis site. Using this technique, another endoscope in the adjacent lumen looks for the light, which diffuses through the lumen wall and projects onto the wall of the adjacent lumen. This light represents the potential intersection anastomosis point. A cap or lens can also be placed over the light emitting endoscope to further intensify and pinpoint the proposed intersection point. A similar technique could use radiowave- or ultrasound-transducers and receivers to collocate the endoscope tips. In some embodiments, a system may include an endoscope having a sensor and a magnetic anastomosis device for deployment using the endoscope.

A third location technique involves magnetic sensing techniques to determine the proximity of the deployed ring magnet in the adjacent lumen. By maximizing the magnetic field being sensed, the minimum distance between the adjacent channels can be identified. The magnetic sensor can be carried on a probe inserted down the working channel of the endoscope and utilize common magnetic sensing technology such as a Hall Effect Sensor or Reed switch.

With trans-illumination and magnetic sensing, an additional accessory may also assist with delivering magnetic devises to a precise anastomosis site. A radially expanding ring structure can be deployed with the endoscope or laparoscope that can press fit and seat itself on the scope's outer diameter. The outer diameter of this expanding element is sized to allow the deployed device to seat itself on this expanding element (again likely a press fit). With this expanding element and magnetic device radially seated about the endoscope axis, the endoscope can be directed to the ideal anastomotic location through direct contact, trans-illumination, or magnetic sensing, and then the mating magnet device released when the anastomosis site is identified.

Figure 6:
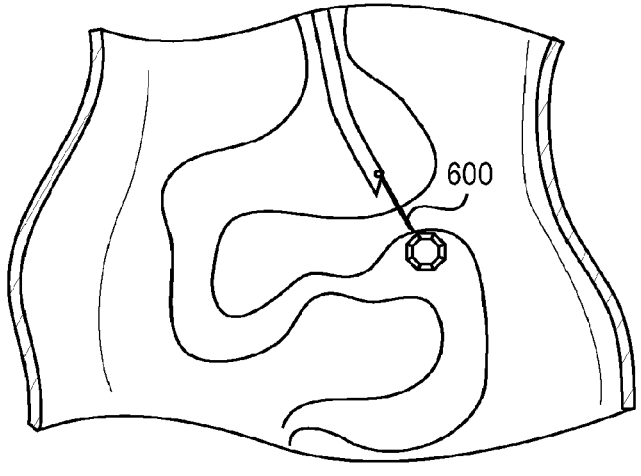
FIG. 6 shows another embodiment of delivery using endoscopic ultrasound guided needle delivery of one magnet assembly into lumen #1 followed by deployment to of the second magnet assembly in lumen #2.

In other embodiments, the self-assembling magnet devices could be delivered using ultrasound guidance, e.g., endoscopic ultrasound. For example, using an echoendoscope in the stomach, a suitable small intestine target could be identified. As shown in FIG. 6, a delivery needle 600 (e.g., an aspiration needle) or catheter can be used to access to the small intestine target and deliver the self-assembling magnets into the small intestine lumen. The delivery can be guided with fluoroscopy or endoscopic ultrasound. Following self-assembly, these small intestine magnets would couple with a second set of magnets deployed in the stomach. The two devices can be delivered with the same needle or with different needles. It is also possible to deliver the first device with an endoscope and the second device with a needle or vice versa.

Figures 7, 8:
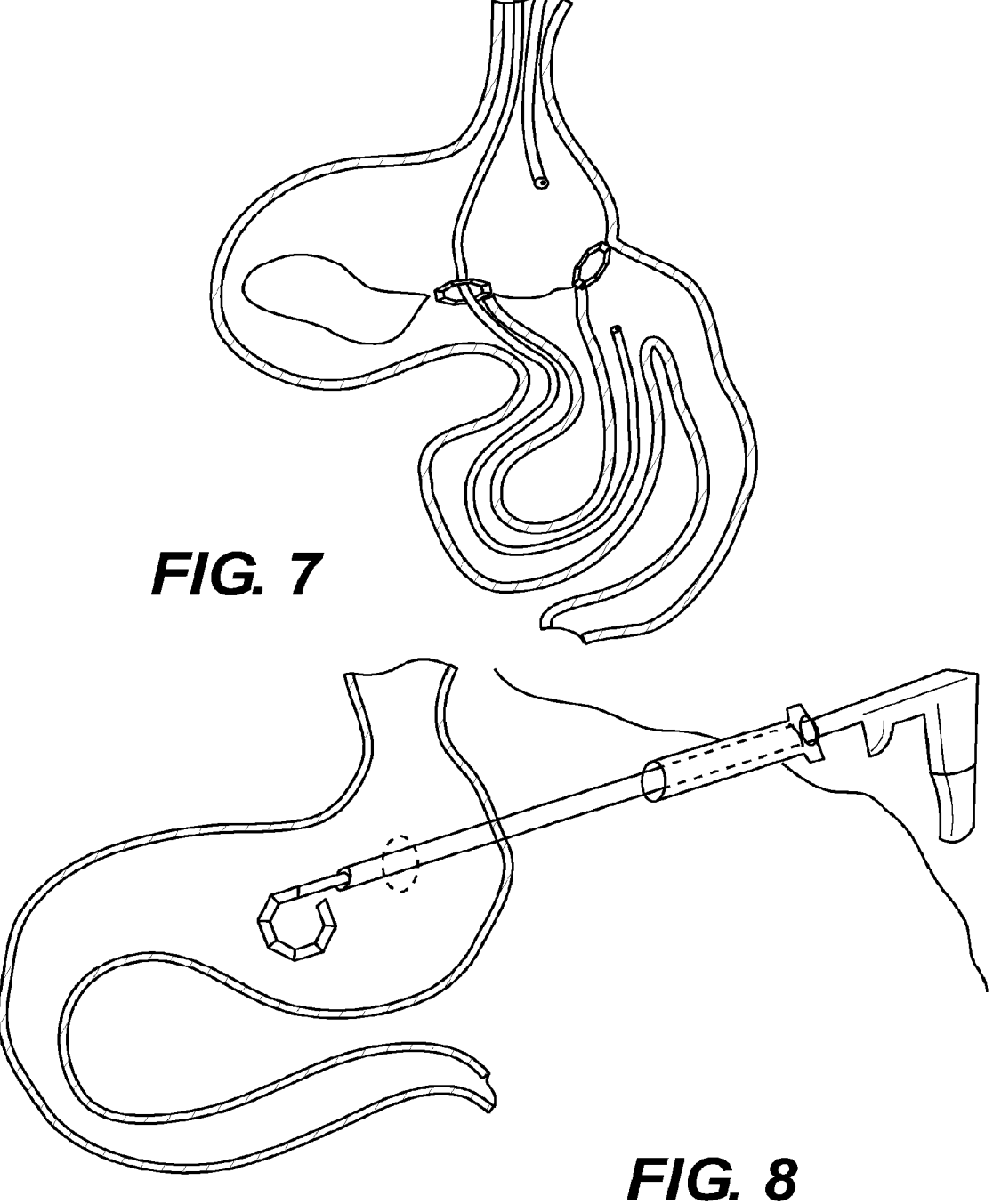
FIG. 7 shows the creation of a preliminary anastomosis to serve as a conduit for deeper endoscope delivery in order to create subsequent multiple anastomoses.
FIG. 8 shows laparoscopic magnet device delivery into a lumen (stomach, in this example).

In another embodiment, illustrated in FIG. 7, a first anastomosis, created in an initial procedure, can be used to provide access for the creation of a second anastomosis. This process could theoretically be repeated multiple times to create additional anastomoses. For example, a gastrojejunal anastomosis (stomach to mid-small intestine) could serve as a conduit for the creation of a second, more distal gastrojejunal anastomosis. Ultimately, in this particular scenario, the stomach would have several bypasses to the small intestine. Additionally, in some instances, more anastomoses could be added to "titrate" to a specific clinical effect (e.g., lower glycosylated hemoglobin in type 2 diabetes). In alternative embodiments, an anastomosis may be placed to give access for a different type of surgery, e.g., tumor removal.

In another embodiment of delivery, the self-assembling magnets could be delivered laparoscopically through a surgical incision into the target organs (e.g., stomach and small intestine) and allowed to couple to create an anastomosis, as shown in FIG. 8. Again, this procedure could be directed with fluoroscopy or ultrasound and the procedure can be purely laparoscopic, or a combination of endoscopic and/or laparoscopic and/or needle procedures.

Gastrointestinal anastomoses can be used to address a number of conditions. An anastomosis or series of anastomoses between the proximal bowel and distal bowel may be used for treatment of obesity and metabolic conditions, such as Type II diabetes and dyslipidemia. The procedure can also be used to induce weight loss and to improve metabolic profiles, e.g., lipid profiles. The bowel includes any segment of the alimentary canal extending from the pyloric sphincter of the stomach to the anus. In some embodiments, an anastomosis is formed to bypass diseased, mal-formed, or dysfunctional tissues. In some embodiments, an anastomosis is formed to alter the "normal" digestive process in an effort to diminish or prevent other diseases, such as diabetes, hypertension, autoimmune, or musculoskeletal disease.

Using the self-assembling magnetic devices as discussed herein, it is possible to create a side-to-side anastomosis that does not require exclusion of the intermediate tissues, as is common with state-of-the-art bariatric procedures. That is, using the devices of the invention (or other means for creating an anastomosis) it is possible to create an alternate pathway that is a partial bypass for fluids (e.g., gastric fluids) and nutrients (e.g., food), while at least a portion of the old pathway is maintained. This design allows the ratio of "normal" to "modified" digestion to be tuned based upon the goals of the procedure. In other words, using the described procedure, a doctor can choose the ratio of food/fluids shunted down the new (partial) bypass versus food/fluids shunted down the old pathway. In most instances, the fraction shunted down the bypass limb will drive the patient toward the desired clinical endpoint (e.g., weight loss, improvement in glycosylated hemoglobin, improvement in lipid profile, etc.) The mechanism by which the endpoints are achieved may involve early macronutrient delivery to the ileum with stimulation of L-cells and increase in GLP-1 production, for example. The mechanism may also involve loss of efficiency of nutrient absorption, especially glucose, thereby reducing blood glucose levels. At the same time, however, the fraction shunted down the old pathway protects against known metabolic complications that can be associated with bariatric surgery such as excessive weight loss, malabsorptive diarrhea, electrolyte derangements, malnutrition, etc.

To achieve a desired ratio of bypass (e.g., re-routing food and secretions to flow down the new pathway, say, 70% or 80% or 90% or 100% of the time), the size, location, and possibly number of anastomoses will be important. For example, for a gastrojejunal anastomosis, it may be critical to place the anastomosis in a dependent fashion to take advantage of the effects of gravity. Also, instead of a round anastomosis, it may be better to create a long, oval-shaped anastomosis to maximize anastomotic size. Alternatively, multiple gastrojejunal anastomoses may be used to titrate to a certain clinical endpoint (e.g., glycosylated hemoglobin in Type II diabetes). Most of the procedures described herein may be used to place one or more anastomoses, as needed, to achieve the desired clinical endpoint. For example, the two endoscope procedures illustrated in FIGS. 4A and 4B can be used to create a partial bypass of a portion of the bowel. Based upon the desired ratio of bypassed and non-bypassed nutrients, the anastomoses shown in FIGS. 4A and 4B can be made larger, e.g., greater than 1 cm in open diameter, or several smaller anastomoses can be placed to achieve the desired ratio.

The procedure is also adjustable. For example, a first anastomosis may be formed and then, based upon clinical tests performed after the procedure, one or more anastomoses can be added to improve the results of the clinical tests. Based upon later clinical results, it may be necessary to add yet another anastomosis. Alternatively, it is possible to partially reverse the condition by closing one or more anastomosis. Because the partially bypassed tissues were not removed, they can return to near normal functionality with the passage of greater amounts of nutrients, etc. The anastomoses may be closed with clips, sutures, staples, etc. In other embodiments, a plug may be placed in one or more anastomoses to limit the ratio of nutrients that traverse the "normal" pathway. Furthermore, it is possible to close an anastomosis in one location in the bowel and then place a new anastomosis at a different location. Thus, is possible to generally and tunably create partial bypasses, or a series of partial bypasses, between portions of the bowel to achieve clinical endpoints, e.g., as described in FIG. 3.

The described procedures may also be used with procedures that remove or block the bypassed tissues, as is common with bariatric procedures. For example, a gastrojejunal anastomosis may be coupled with a pyloric plug (gastric obstruction) or another closure of the pylorus (e.g., sutured closure) to shunt food completely down the new bypass. Such procedures can be used, for example, to bypass tissue that is diseased, e.g., because of cancer.

In another category of procedures, endoscopic ultrasound (EUS) can be used to facilitate guided transgastric or transduodenal access into the gallbladder for placement of a self-assembling magnetic anastomosis device. Once gallbladder access is obtained, various strategies can be employed to maintain a patent portal between the stomach and the gallbladder or the duodenum and the gallbladder. In another embodiment, gallstones can be endoscopically retrieved and fluid drained. For example, using the described methods, an anastomosis can be created between the gallbladder and the stomach. Once the gallbladder is accessed in a transgastric or transduodenal fashion, the gallstones can be removed. Furthermore, the gallbladder mucosa can be ablated using any number of modalities, including but not limited to argon plasma coagulation (APC), photodynamic therapy (PDT), sclerosant (e.g., ethanolamine or ethanol).

Figure 9A:
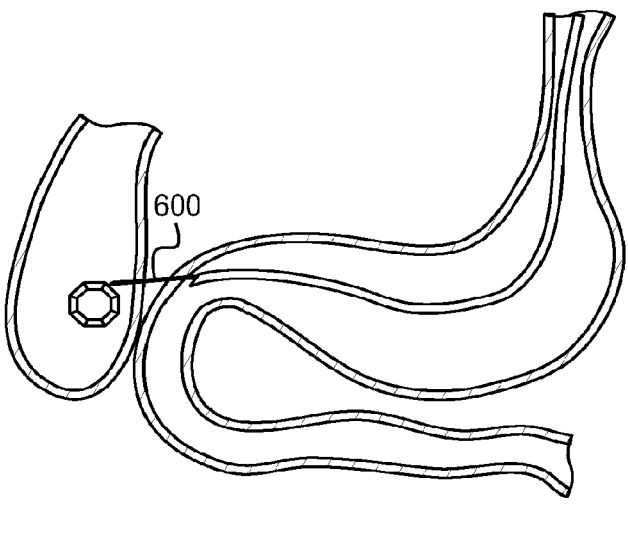
FIG. 9A shows endoscopic ultrasound guided needle delivery of a magnet assembly into the gallbladder.
Figure 9B:
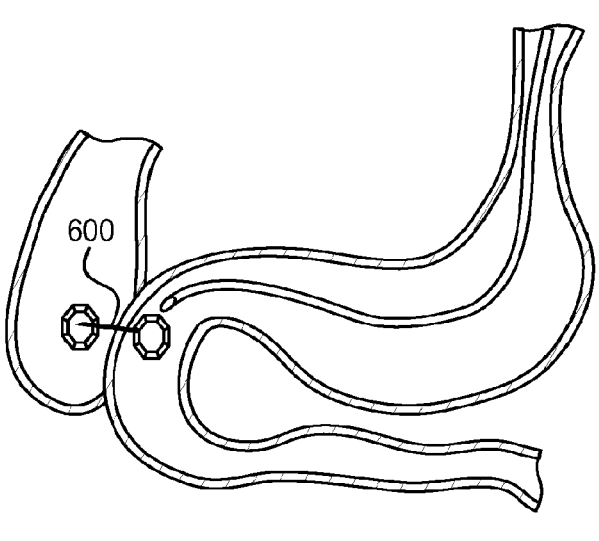
FIG. 9B shows coupling of the magnet assembly from FIG. 9A coupled with a second magnet assembly in the stomach or duodenum.

One strategy for creation of a portal is to deploy self-assembling magnets via an endoscopic needle under ultrasound guidance into the gallbladder and also into the stomach or duodenum. These magnets will mate and form a compression anastomosis or fistula. A second strategy for creation of a portal is to deploy self-assembling magnets via an endoscopic needle 600 as shown in FIGS. 9A and 9B. While the coupled magnetic assemblies are shown as octagons, the closed frame could take the shape of any polygonal structure, e.g., a square, a circle, a triangle, hexagon, heptagon, nonagon, decagon, dodecagon, etc. One such device would be deployed into the gallbladder, and the mating device would be deployed into the stomach or duodenum. In the same fashion as discussed above with respect to gastrointestinal deployment, the tissue circumscribed by the two magnetic devices can be cut with cautery, microscalpel, needle-knife, or other deployable cutting mechanism. In another embodiment, the coupled tissues can be left to necrose and form the anastomosis.

Figure 10:
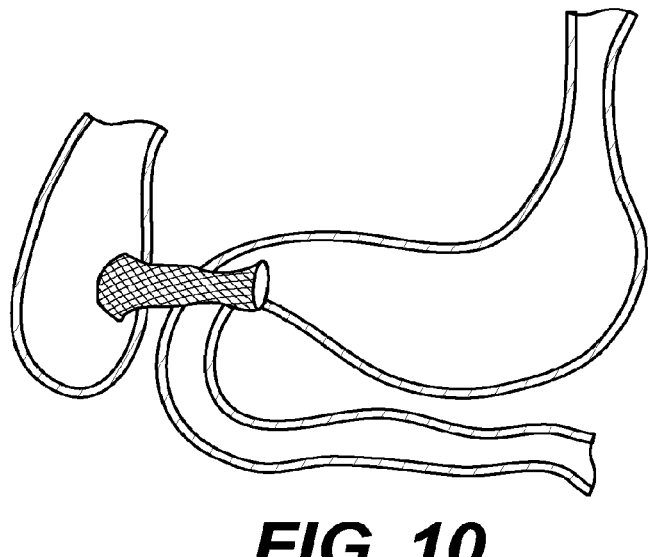
FIG. 10 shows stent deployment between the gallbladder and either the stomach or duodenum.
Figure 11:
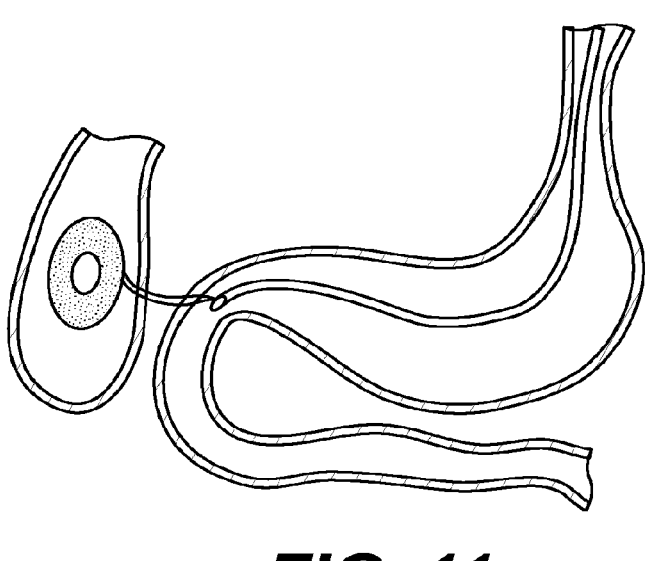
FIG. 11 shows another embodiment of an intra-gallbladder magnet assembly that is a balloon that fills with fluid, gas, or magnetic material. This balloon is tethered to the endoscope and is initially delivered through an endoscopic ultrasound guided needle.

The devices need not be limited to forming holes, however. Other structures can be coupled to one or more mating magnetic devices to created additional functionality. For example, a stent could be deployed between tissues, such as the gallbladder and the stomach, as shown in FIG. 10. Alternatively, the gallbladder magnet could be coupled to a balloon-based device that fills with air, fluid, magnetic pieces or magnetic particles. Upon inflation, the balloon would serve as an anchor in the bile duct following placement. The balloon could also have an annular configuration to allow for immediate access after coupling with the second magnet. Sec, e.g., FIG. 11. Regardless of embodiment, however, it is critical to contain the original access pathway within the confines of the coupled magnets, i.e., not leaving a pathway for the escape of bile. Otherwise, the opening will allow bile leakage that can result in peritonitis.

Another medical application for self-assembling magnets is direct biliary access. Currently, to achieve decompression for a malignant biliary stricture, endoscopic retrograde cholangiopancreatography (ERCP) is performed. The biliary tract is accessed endoscopically through the papilla in retrograde fashion and a stent is deployed across the stricture over a guidewire. These stents frequently require subsequent procedures for exchange, clean-out, or placement of additional overlapping stents. The need for exchange and cleaning is required to counteract the high rate of infection of the biliary tree (i.e. cholangitis) when using an ERCP procedure. Because of the high rate of morbidity, ERCP is typically limited to patients that have no other option to address pancreatic disease.

Using devices of the invention, however, it is possible to easily form an anastomosis between the bile duct (preferably the main bile duct) and either the duodenum or the stomach (choledocho-gastric and choledocho-duodenal anastomoses, respectively). This anastomosis is permanent and typically does not require intervention if located apart from the diseased tissue. In an embodiment, a biliary magnetic device is delivered directly into the bile duct under endoscopic ultrasound guidance. As described below, the self-assembling magnetic device is extruded through a needle or catheter, whereupon it deploys in the correct configuration. Using fluoroscopy or ultrasound, it is then possible to confirm that the device has self-assembled and is in the correct location. In some embodiments, the magnetic device may be tethered to the delivery needle or catheter by means of a detachable wire or suture to enable mechanical retraction until optimal positioning is confirmed.

Figures 12, 13:
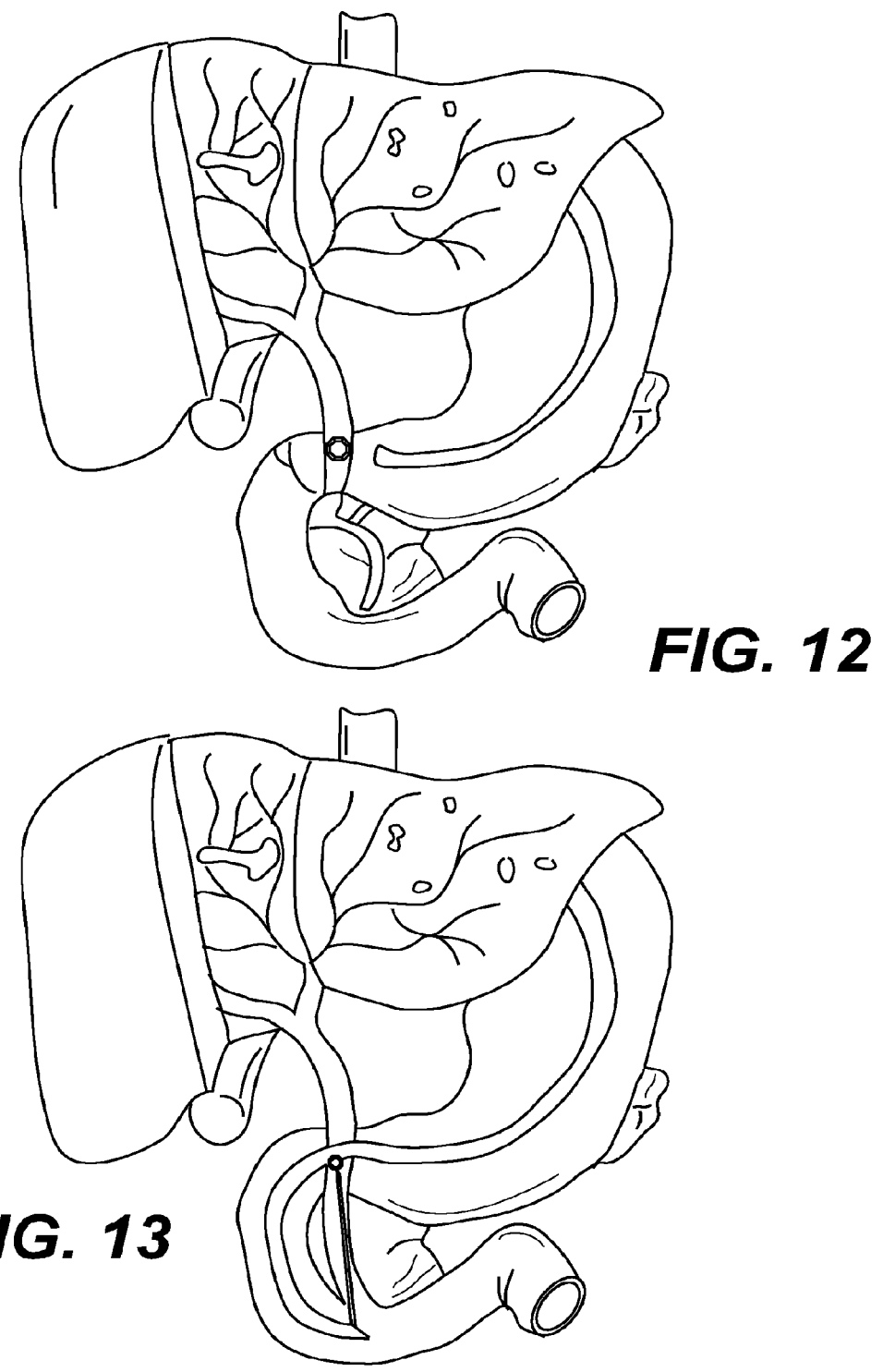
FIG. 12 shows endoscopic ultrasound guided needle delivery of a magnet assembly into the bile duct.
FIG. 13 shows magnet assembly delivery into the bile duct through endoscopic retrograde cholangiopancreatography techniques.
Figures 14, 15:
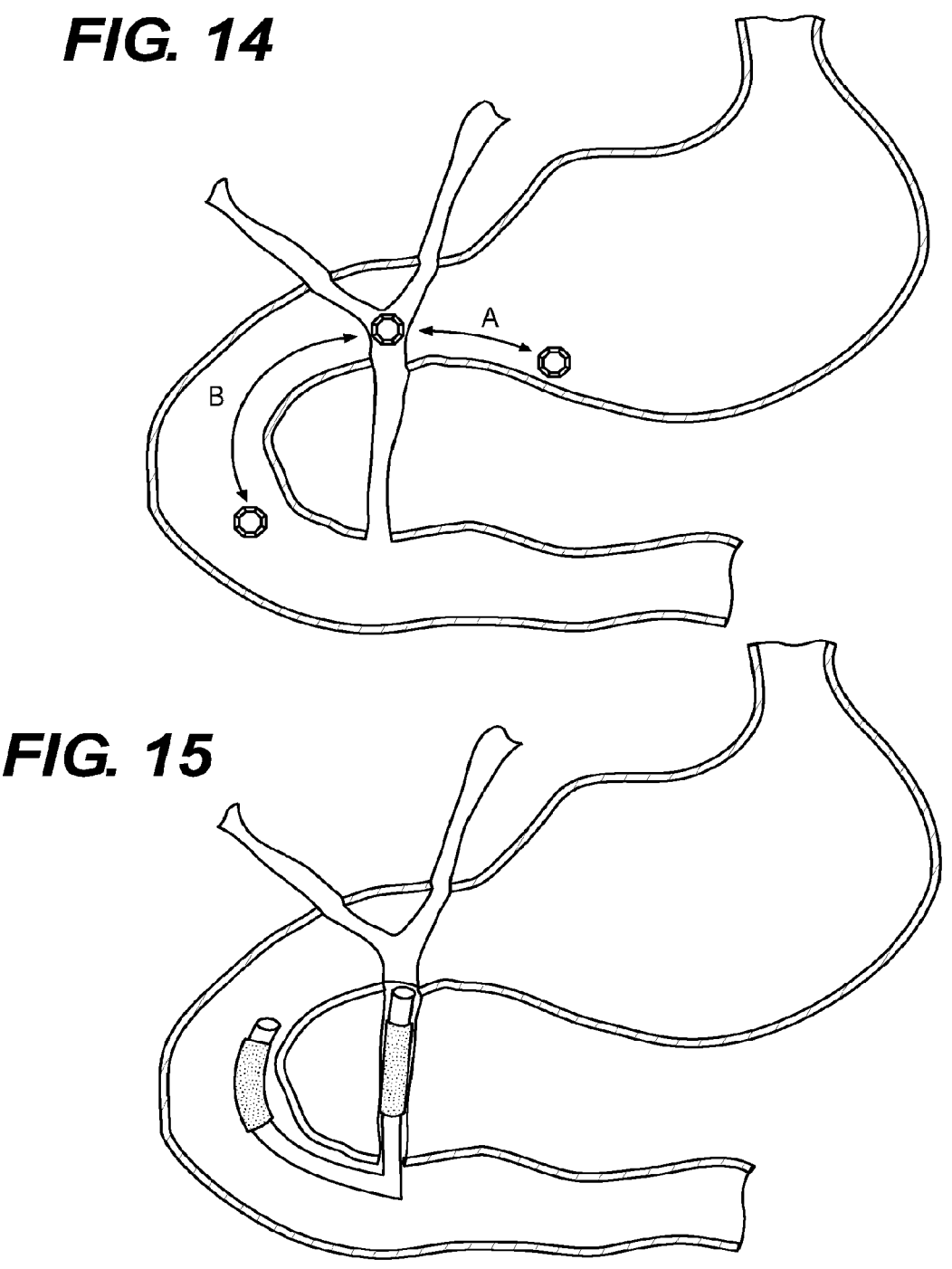
FIG. 14 shows coupling of the intra-bile duct magnet assembly with a second magnet assembly deployed either in the stomach (A) or duodenum (B).
FIG. 15 shows another embodiment of bile duct magnetic anastomosis in which a hinged magnetic bile duct stent swings back onto itself by magnetic attraction to form an anastomosis between the bile duct and duodenum.

In one embodiment, the magnetic device can be delivered endoscopically to the bile duct via wall of the duodenum, as shown in FIG. 12. In another embodiment, the biliary magnet can be delivered in conventional retrograde fashion through the ampulla into the bile duct, as shown in FIG. 13. One benefit of retrograde delivery is that it avoids needle punctures across tissue planes, as is the case with the deployment method shown in FIG. 12. Regardless of the method for delivering the biliary magnets, however, a second magnetic device is required in either the gastric (A) or duodenal (B) lumen, as shown in FIG. 14. Typically, this decision is dependent upon the patient's anatomy (e.g., size of the duodenal lumen) and the location of the initial biliary magnet. In scenarios based on endoscopic ultrasound needle delivery, the second magnetic device can be connected to the biliary magnet via the aforementioned detachable wire, and therefore extruded through the same delivery needle/catheter. Alternatively, the second device can be pre-attached to the exterior of the endoscope and slid into position for coupling after biliary magnet deployment. The latter procedure may be more applicable to forward-viewing echoendoscopes but may be used with endoscopes, generally.

In another embodiment, the biliary magnet is a balloon-based device that fills with air, fluid, magnetic pieces or magnetic particles, similar to previously described with respect to gallbladder procedures. Upon inflation, the balloon would serve as an anchor in the bile duct following placement. In an embodiment, the balloon could have an annular configuration to allow for immediate access after coupling with the second magnet. Additionally, like the gallbladder procedures described above, a biliary magnetic device can be used with a stent form-factor. In an embodiment, the stent has an internal biliary magnet and a hinged external magnet. The stent can be inserted in retrograde fashion through the ampulla into the bile duct. The hinged external magnet can then be swung around and coupled with the internal biliary magnet to form a fistula between the bile duct and the duodenum, as shown in FIG. 15.

Figure 16:
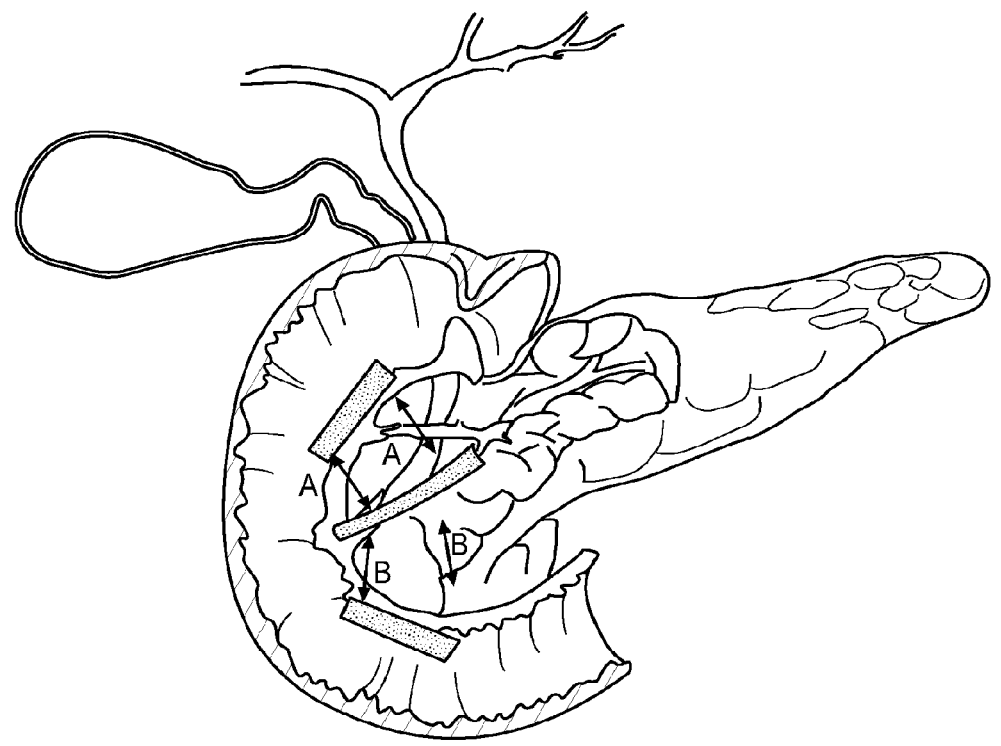
FIG. 16 shows a magnetic stent that can be delivered into the pancreatic duct. The stent can be coupled with a magnet in the stomach (A) or in the duodenum (B) to create a drainage anastomosis for the pancreatic duct.

The magnetic devices of the invention can also be used to treat pancreatic diseases. For example, the pancreatic duct requires decompression in certain disease states, such as chronic pancreatitis. Currently, extensive pancreatic duct decompression requires surgery (e.g., Peustow surgery in which the pancreas is filleted along the axis of the pancreatic duct and connected to a loop of small intestine for improved pancreatic drainage). As an alternative to Peustow surgery, extensive pancreatic duct decompression can be accomplished via creation of a large magnetic compression anastomosis between the pancreatic duct and either the stomach or duodenum using a magnetic pancreatic catheter, as shown in FIG. 16. The catheter can be magnetic along its entire length or only at certain intervals. The catheter can be in the form of a stent or straw. The pancreatic duct can be accessed using conventional ERCP methods (retrograde cannulation through the ampulla) or by direct needle access using endoscopic ultrasound (EUS). The magnetic pancreatic catheter can be delivered into the pancreatic duct and coupled with a second magnetic device in either the stomach or duodenum. As in the biliary scenario described above, the magnetic pancreatic catheter could be hinged to the second magnetic device.

Figure 17:
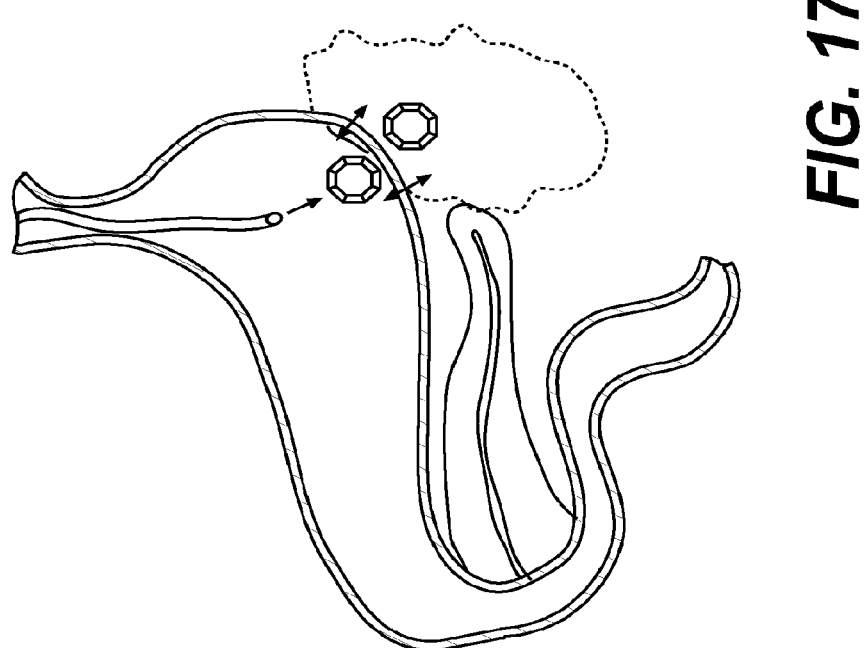
FIG. 17 shows a magnetic assembly that is delivered into a peripancreatic collection (dotted structure) using endoscopic ultrasound guided needle/catheter delivery which then couples with a second magnet assembly deployed in the stomach.

Self-assembling magnetic devices can also be used to access and drain fluid collections located adjacent to the gastrointestinal tract, as shown in FIG. 17. For example, following a bout of pancreatitis, pancreatic fluid collections can form that require drainage. While drainage can be accomplished using surgery or a percutaneous catheter, endoscopic drainage has been found to be more clinically and cost-effective, but can be complicated by bleeding, perforation, and/or inadequate drainage. As an alternative to surgical draining, magnetic devices of the invention can be delivered through a needle or sharpened catheter into the collection under endoscopic ultrasound (EUS) guidance, as shown in FIG. 17. Following assembly, the first magnetic device is coupled to the second magnetic device that has been placed in the gastrointestinal lumen (e.g. stomach). In order to speed removal after drainage, the first magnet may be tethered by a connecting wire as previously described. As described previously, the intervening tissue can be cut using electrocautery or dilation followed by needle and wire access. Additional devices, such as magnetic coupling clamps can be used to control blood flows to allow for "blood-less" endoscopic entry into the collection.

Figure 18:
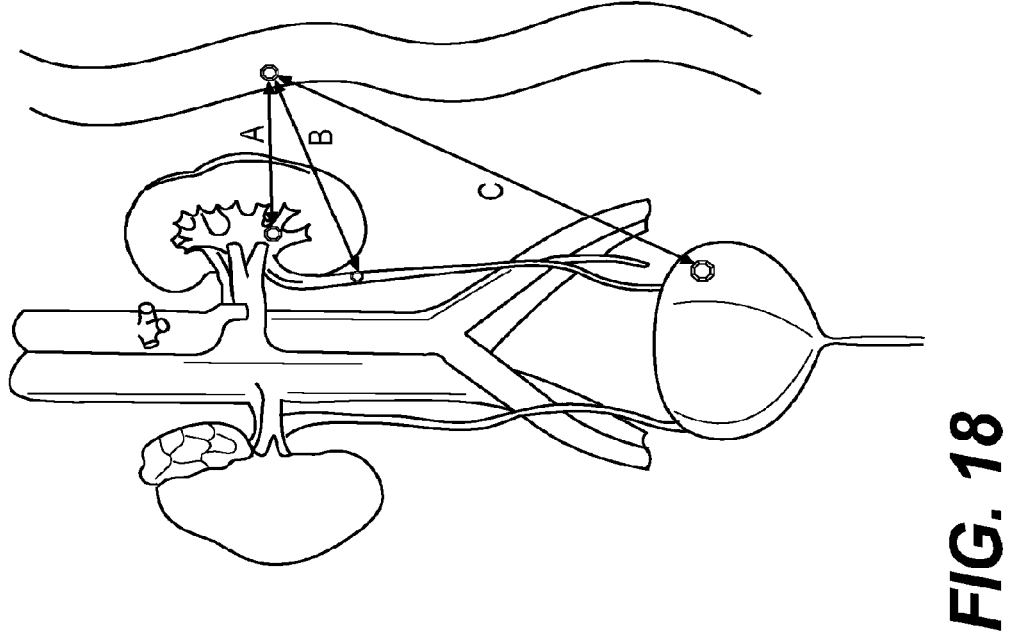
FIG. 18 shows different targets for anastomoses between the urinary system and the gastrointestinal system: renal calyx (A), ureter (B), and bladder (C).

Self-assembling magnets can also be used for urological applications such as forming bypasses to treat an obstructed urogenital tract, as shown in FIG. 18. For example, a magnetic anastomosis could be created between the renal calyx and bowel (A), between the ureter and bowel (B), or between the bladder and bowel (C). Self-assembling magnetic devices of the invention can be delivered into the urological tract using an endoscope, laparoscope, or needle, as described above. The reciprocal magnetic device could be delivered into the gastrointestinal tract using an endoscope, laparoscope, or needle as previously described. In other embodiments, the devices can be used for reproductive procedures, such as bypassing a portion of obstructed fallopian tube or bypassing a vasectomy.

Figure 19:
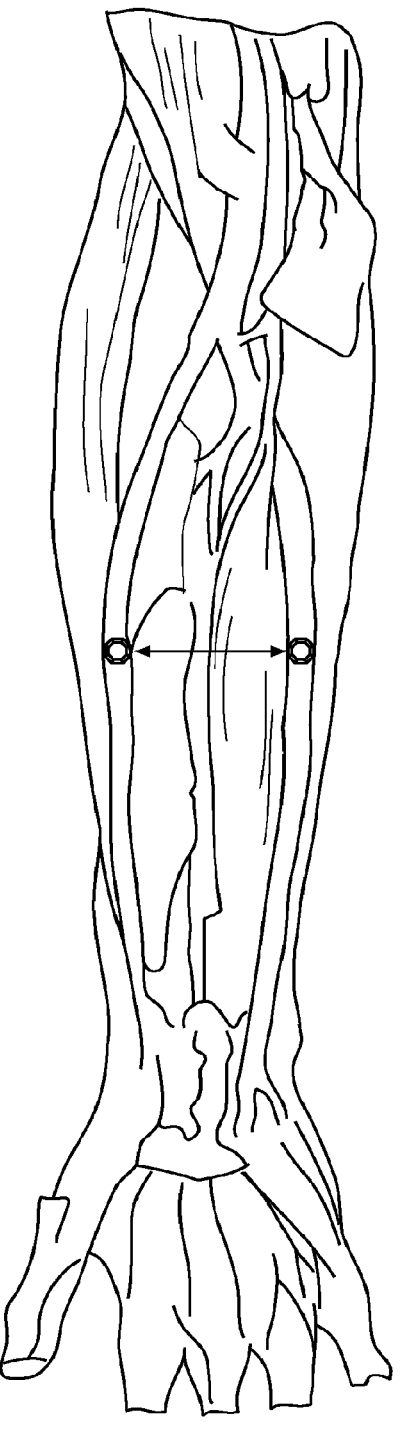
FIG. 19 shows magnet assemblies in adjacent blood vessels to couple and create a vascular anastomosis.

In yet another application, self-assembling magnetic devices can be used to create vascular anastomoses or to treat cardiac conditions. For example, a magnetic anastomosis coupling can be formed between adjacent blood vessels with magnetic devices, as shown in FIG. 19. In an embodiment, the self-assembling devices can be delivered with a vascular delivery device, such as a catheter. Additionally, as described above with respect to gallbladder and pancreatic applications, a shunt can be installed to bypass a portion of the vasculature that is weak or blocked.

Figure 20:
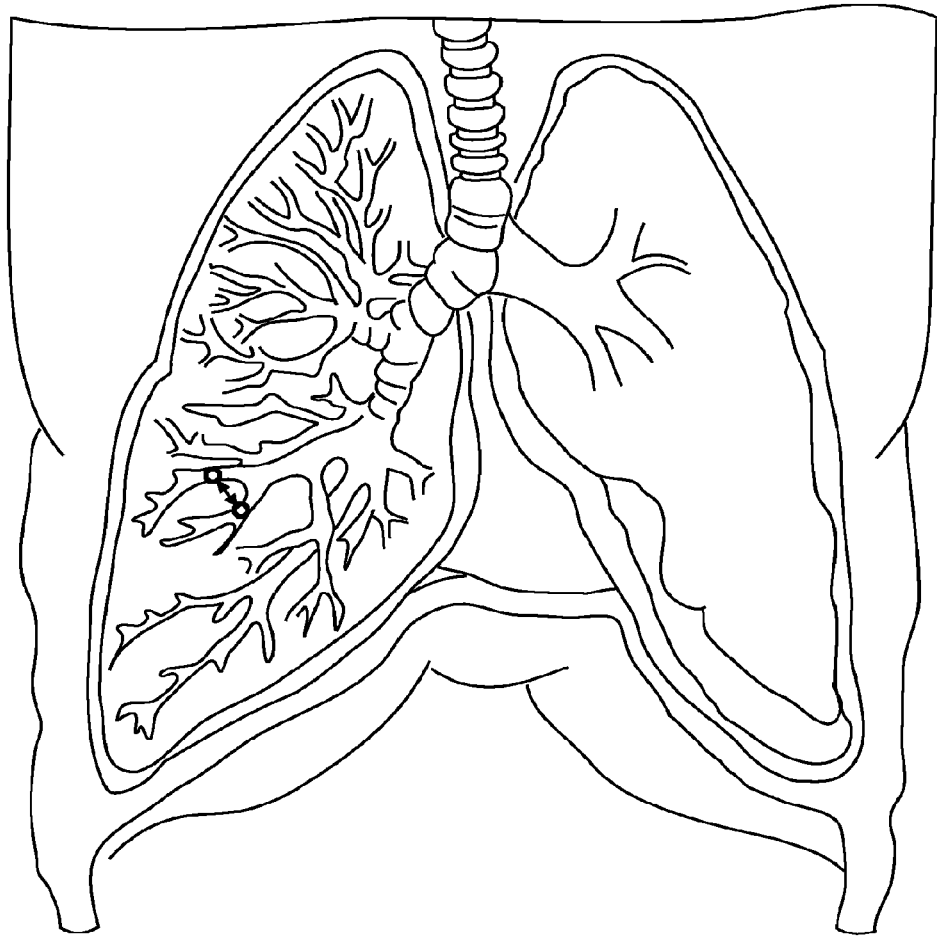
FIG. 20 shows magnet assemblies in different parts of the respiratory system to create anastomoses between adjacent bronchioles.

Self-assembling magnets can also be used for pulmonary applications such as forming bypasses in the airway to treat chronic obstructive pulmonary disease (COPD). For example, magnetic anastomoses can be created by deploying self-assembling magnetic devices into adjacent bronchioles, as shown in FIG. 20. Creation of pulmonary "bypasses" could lower airway resistance that characterizes respiratory diseases such as COPD.

Figure 21:
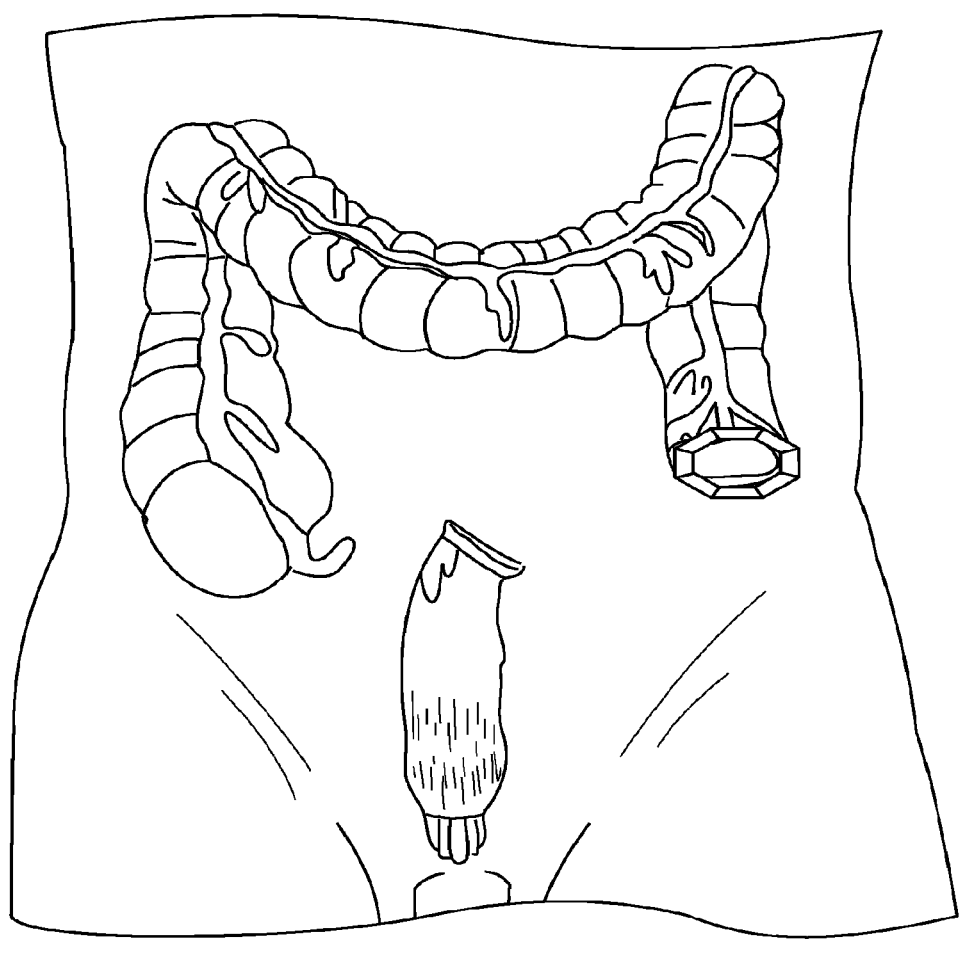
FIG. 21 shows an external magnet assembly and an internal magnet assembly within the gastrointestinal tract used to create a surgical stoma for fecal drainage.

Self-assembling magnetic devices can also be used to create surgical stomas for diversion of a fecal stream, e.g., into a colostomy bag. For example, a magnetic anastomosis can be created by deploying self-assembling magnets into the gastrointestinal tract (e.g. large intestine), as shown in FIG. 21, and then coupling the interior magnet to an external magnet worn and secured at the level of the skin. The exterior magnetic device may be coupled to yet a third magnetic device that is coupled to a collection device. Such a system allows easy removal of the collection device for cleaning, etc.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Various inventive concepts may be embodied as one or more methods, of which examples have been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

As used herein in the specification and in the claims, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Without limitation, potential subject matter that may be claimed (prefaced with the letter "P" so as to avoid confusion with the actual claims presented below) includes:

P1. An apparatus for guiding magnetic anastomosis devices, the apparatus comprising a metal cord configured to fit within a catheter having a distal end and a proximal end, wherein the distal end is bent at a 180° angle, such that the distal end of the metal cord is pointed toward the proximal end, forming a bent portion of the metal cord; wherein the bent portion of the metal cord is configured to engage a magnetic anastomosis device; wherein a first pulling force on the metal cord is greater than a second force needed to unbend the metal cord outside of the catheter; wherein the first pulling force is less than a third force needed to unbend the metal cord inside of the catheter due to a friction force between the metal cord and a catheter wall.

P2. The apparatus as described in innovation P1, wherein the metal cord is less than or equal to 1.8 mm in diameter.

P3. The apparatus as described in any prior innovation, wherein the friction force is reduced to zero when the bent portion of the metal cord is disengaged from the catheter.

P4. The apparatus as described in any prior innovation, wherein the bent portion is unbent in order to disengage the magnetic anastomosis device.

P5. The apparatus as described in any prior innovation further comprising: a first ferrule configured to engage with the distal end of the metal cord such that the metal cord and ferrule are engaged with the catheter wall.

P6. The apparatus as described in any prior innovation further comprising a second ferrule configured to engage with the magnetic anastomosis device so as to maintain the magnetic anastomosis device within the catheter.

P7. The apparatus as described in any prior innovation further comprising a first magnet attached to a proximal end of the first ferrule; and a second magnet attached to a distal end of the second ferrule.

P8. The apparatus as described in any prior innovation wherein a string on the magnetic anastomosis device comprises a first hook, and the second ferrule comprises a second hook wherein the first hook and the second hook are configured to interlock.

Although the above discussion discloses various exemplary embodiments of the invention, it should be apparent that those skilled in the art can make various modifications that will achieve some of the advantages of the invention without departing from the true scope of the invention. Any references to the "invention" are intended to refer to exemplary embodiments of the invention and should not be construed to refer to all embodiments of the invention unless the context otherwise requires. The described embodiments are to be considered in all respects only as illustrative and not restrictive.

What is claimed is:

1. A system comprising:
a catheter;
a first cord having a proximal end and a distal end configured to fit within the catheter;
a first ferrule at the distal end of the first cord;
a second cord having a distal end and a proximal end, the distal end and the proximal end configured to engage a magnetic anastomosis device, the second cord having a portion in which the second cord is bent substantially 180° back toward the distal end, the portion configured to fit within the catheter and including a second ferrule configured to contact the first cord within the catheter.

2. The system of claim 1, wherein:
the first ferrule includes a first magnet at a proximal end of the first ferrule; and
the second ferrule includes a second magnet at a distal end of the second ferrule for magnetic engagement with the first magnet to allow manipulation of the engaged device via the first cord and separation of the second cord from the first cord by overcoming the magnetic engagement between the first and second magnets.

3. The system according to claim 1, wherein at least one of the first cord or the second cord is less than or equal to 1.8 mm in diameter.

4. The system according to claim 1, wherein the bent portion of the second cord is able to hold a magnetic device or devices with a tensile strength of 0-10 pounds.

5. The system according to claim 1, wherein the first cord and first ferrule are configured such that the first ferrule engages with an inner wall of the catheter when the first and second ferrules are within the catheter.

6. The system according to claim 1, wherein the first cord is a metal cord.

7. The system according to claim 1, wherein the first cord is a suture.

8. The system according to claim 1, wherein the second cord is a metal cord.

9. The system according to claim 1, wherein the second cord is a suture.

10. The system according to claim 1, wherein the catheter is an endoscope having a 3.7 mm working channel or less.

11. The system according to claim 1, wherein the catheter is a laparoscopic delivery device.

12. The system according to claim 1, further comprising the magnetic anastomosis device.

13. The system according to claim 12, wherein the magnetic anastomosis device is a self-assembling magnetic anastomosis device having a plurality of magnetic segments.

14. The system according to claim 13, wherein the magnetic anastomosis device self-assembles into a polygon configuration.

15. The system according to claim 13, wherein the magnetic anastomosis device self-assembles into a circle configuration.

16. The system according to claim 13, wherein the self-assembling magnetic anastomosis device is configured to be delivered via the catheter.

17. The system according to claim 12, wherein the magnetic anastomosis device is a solid anastomosis device.

* * * * *